United States Patent
Schulte et al.

(10) Patent No.: US 8,632,448 B1
(45) Date of Patent: Jan. 21, 2014

(54) PROTON SCATTERING ANALYSIS SYSTEM

(75) Inventors: Reinhard W. Schulte, Grand Terrace, CA (US); Vladimir A. Bashkirov, Moreno Valley, CA (US)

(73) Assignee: Loma Linda University Medical Center, Loma Linda, CA (US)

( * ) Notice: Subject to any disclaimer, the term of this patent is extended or adjusted under 35 U.S.C. 154(b) by 650 days.

(21) Appl. No.: 12/701,417

(22) Filed: Feb. 5, 2010

Related U.S. Application Data

(60) Provisional application No. 61/150,265, filed on Feb. 5, 2009.

(51) Int. Cl.
*A61N 5/10* (2006.01)

(52) U.S. Cl.
USPC .............................. 600/1; 378/204; 378/205

(58) Field of Classification Search
USPC .................................. 600/1, 2; 378/204, 205
See application file for complete search history.

(56) References Cited

U.S. PATENT DOCUMENTS

| | | | | |
|---|---|---|---|---|
| 2005/0109939 | A1* | 5/2005 | Engler et al. | 250/336.1 |
| 2006/0259282 | A1* | 11/2006 | Failla et al. | 703/2 |
| 2007/0181815 | A1* | 8/2007 | Ebstein | 250/370.11 |

* cited by examiner

*Primary Examiner* — Christine Matthews
*Assistant Examiner* — Joshua D Lannu
(74) *Attorney, Agent, or Firm* — Knobbe, Martens, Olson & Bear LLP

(57) ABSTRACT

Disclosed are systems and methods for characterizing interactions or proton beams in tissues. In certain embodiments, charged particles emitted during passage of protons, such as those used for therapeutic and/or imaging purposes, can be detected at relatively large angles. In situations where beam intensity is relatively low, such as in certain imaging applications, characterization of the proton beam with charged particles can provide sufficient statistics for meaningful results while avoiding the beam itself. In situations where beam intensity is relatively high, such as in certain therapeutic applications, characterization of the proton beam with scattered primary protons and secondary protons can provide information such as differences in densities encountered by the beam as it traverses the tissue and dose deposited along the beam path. In certain situations, such beam characterizations can facilitate more accurate planning and monitoring of proton-based therapy.

18 Claims, 24 Drawing Sheets

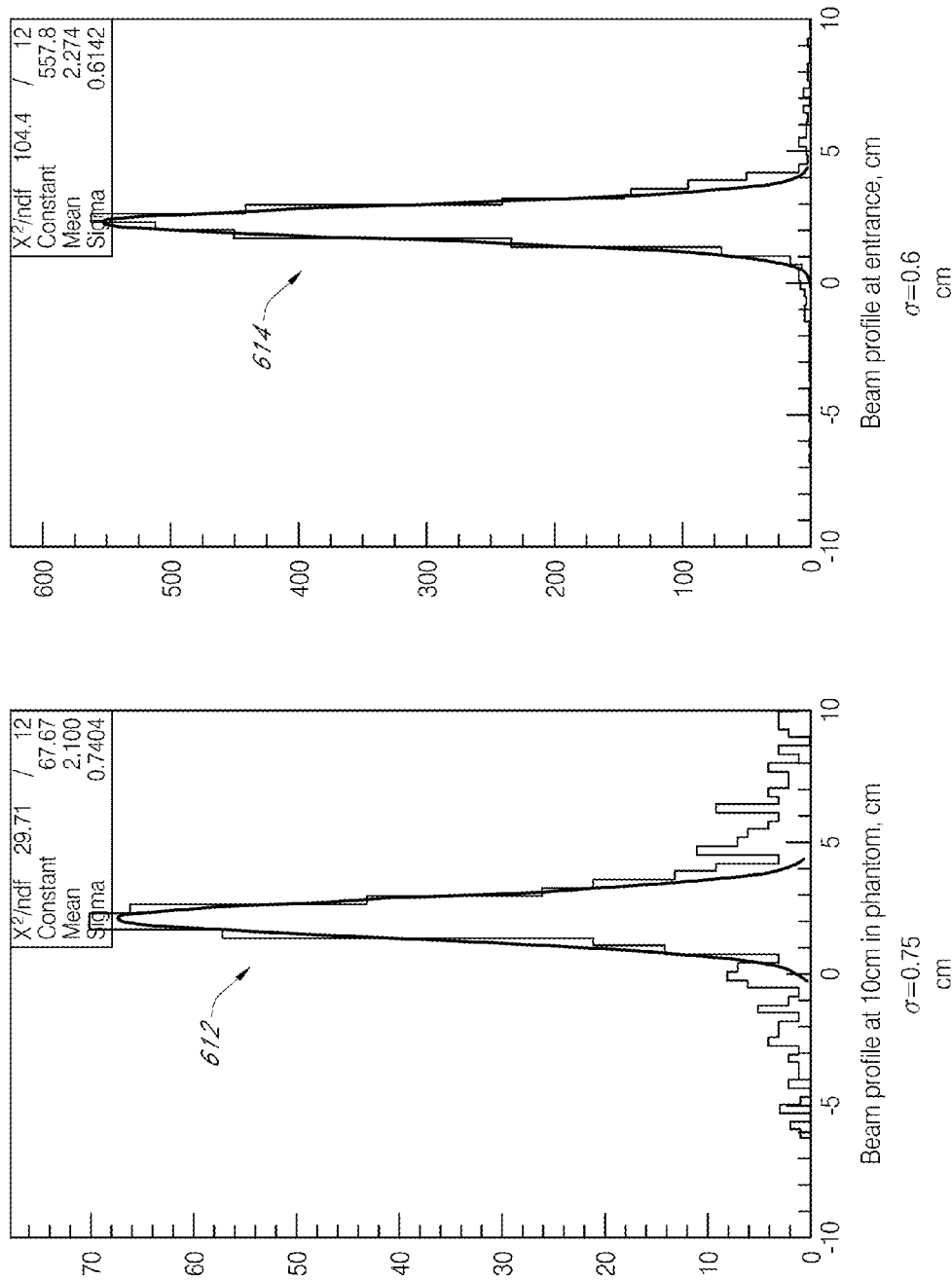

PROTON SCATTERING ANALYSIS SYSTEM

CROSS-REFERENCE TO RELATED APPLICATIONS

This application claims the benefit of priority under 35 U.S.C. §119(e) to U.S. Provisional Application No. 61/150,265, filed on Feb. 5, 2009, entitled "PROTON SCATTERING ANALYSIS SYSTEM," the entirety of which is incorporated herein by reference.

BACKGROUND

1. Field

The invention relates to the field of radiation therapy and to systems and methods for analyzing interactions of protons with tissue or other materials for imaging and to improve diagnosis and accuracy of therapy delivery.

2. Description of the Related Art

Proton beam therapy has known and potential benefits in treatment of a wide variety of disease conditions. Protons at certain energies exhibit a useful characteristic of a relatively high degree of controllability and selective transfer of energy to target tissue with relatively low undesired transfer of energy to non-target tissue. Protons exhibit the physical characteristic of a Bragg peak where a substantial fraction of the energy of a beam of accelerated protons is delivered within a relatively narrow penetration depth and where the depth can be selected and controlled based on the characteristics of material through which the proton beam passes and the energy of the protons. The highest energy deposition per unit length (LET) is typically exhibited at the end of range of such a proton beam, e.g. at the Bragg peak, and this also corresponds to the region of maximum absorbed dose. The characteristics of protons result in a relatively low entrance dose to non-target tissue upstream of the target region and a relatively low (approaching negligible) exit dose (e.g. to non-target tissue downstream from the target region with proper selection of beam energies).

This feature allows a clinician to adjust the proton energy such that the depth of the Bragg peak coincides with the spatial location of target tissue. In many applications, a collimator is used to control the focus of the proton beam. A focused proton beam can be raster scanned and/or modulated to deliver a selected radiation dose to a distributed target region with significantly reduced undesired transfer of energy to non-target tissues, for example as occurs with photonic radiation therapy.

It will be understood however that calculation of an appropriate proton dose and selection of beam energy to achieve a desired depth or range is dependent on accurate knowledge of the characteristics of the materials through which the beam will pass. In some implementations, x-ray imaging and/or computed tomography (CT) is utilized to obtain indications of the internal structures and compositions of the patient, including the intended target region of the proton therapy and intervening non-target tissue. However, inaccuracies and/or uncertainties can arise in images that are based on electron density distributions, thereby leading to corresponding uncertainties in dose and proton range values.

SUMMARY

In certain embodiments, the present disclosure relates to a proton therapy system having a support device configured to support a volume of tissue and expose at least a portion of the volume of tissue to a beam of protons. The beam of protons is configured for therapeutic treatment of at least a portion of the volume of tissue, with the beam of protons defining a beam axis extending through the volume of tissue. The system further includes a charged particle detector disposed relative to the volume of tissue and configured so as to detect charged particles resulting from interactions of the beam of protons with the volume of tissue. The charged particle detector has an acceptance range about a detector axis that extends through a selected location in the volume of tissue and along the beam axis, and the detector axis forms an angle with respect to a forward direction of the beam axis. The angle is within a range of approximately 20 degrees to 90 degrees. The charged particle detector is configured to facilitate reconstruction of tracks associated with the detected charged particles, and the detection results in generation of signals. The system further includes a computing device in communication with the detector and configured to receive the signals and generate data having information that allows the reconstruction of the tracks so as to allow estimation of locations of the interactions in the volume of tissue.

In certain embodiments, the present disclosure relates to a method for planning a proton therapy. The method includes positioning a patient on a support device so as to allow exposure of a portion of the patient to a beam of protons that is configured for therapeutic treatment and travelling generally along a beam path within the patient. The method further includes delivering one or more spills of protons to the patient, with each spill having an intensity associated with the therapeutic beam of protons. The method further includes determining a profile of the beam path based on interaction of the spill of protons in the patient. The profile includes scattering locations of primary protons associated with the spill of protons and vertex locations of secondary protons emitted from within the patient. The profile provides information about differences in densities along the beam path. The primary and secondary protons are detected and characterized at an angle relative to the beam path, with the angle being within a range of approximately 20 degrees to 90 degrees. The method further includes adjusting the beam configuration based on the detected profile.

In certain embodiments, the present disclosure relates to a method for monitoring a proton therapy. The method includes positioning a patient on a support device so as to allow exposure of a portion of the patient to a beam of protons that is configured for therapeutic treatment and travelling generally along a beam path within the patient. The method further includes delivering one or more spills of protons to the patient. The method further includes detecting interactions of the spill of protons in the patient. The detected interactions include scattering locations of protons from within the patient. The detected interactions provide information about numbers of scattering protons at the locations. The protons are detected at an angle relative to the beam path, with the angle being within a range of approximately 20 degrees to 90 degrees. The method further includes estimating a dose deposited for the spill of protons based on the numbers of scattering protons at the locations.

In certain embodiments, the present disclosure relates to a proton based imaging and therapy system. The system includes a support device configured to support a patient and expose at least a portion of the patient to a beam of protons that is configurable for a therapy mode and an imaging mode, with the beam of protons defining a beam axis extending through the patient. The system further includes a charged particle detector mounted to a mounting mechanism so as to allow positioning of the detector at first and second positions relative to the beam axis. The first position is downstream of the patient along the beam axis, and the second position is at an angle θ with respect to the beam axis. The angle θ is within a range of approximately 20 to 90 degrees. The detector is configured so as to detect charged particles resulting from interactions of the beam of protons with the patient. The system further includes a control system configured to position the detector at the first position and deliver the beam of protons in the imaging mode when the proton based imaging and therapy system is being operated for imaging purpose, and to position the detector at the second position and deliver the beam of protons in the therapy mode when the proton based imaging and therapy system is being operated for therapy purpose.

Certain embodiments of the present disclosure provide improved ability to monitor and analyze interaction between an incident proton beam and target tissue as well as a spatial location of a proton beam. Embodiments include a system for determining positions in space, including through patient tissue, through which accelerated protons pass and to utilize this information to mathematically reconstruct an initial or nominal path from which protons can become deflected. The system can also be capable in addition or as an alternative to measure an impact energy and thereby determine an energy loss of an incident proton. Embodiments can determine indications of the elemental or atomic number constitution of material that the proton has impacted. Embodiments provide to the clinician a measured confirmation of an actual path of a proton beam independent of any other aiming or predictive measures.

One embodiment includes, a proton therapy system for delivery of a therapeutic proton beam comprising a plurality of protons towards a target region of a patient, the proton therapy system comprising a patient support configured for supporting a patient, a proton source for generating a therapeutic proton beam, a proton delivery device configured to receive the therapeutic proton beam from the proton source and direct the therapeutic proton beam at a mean initial energy along an initial path towards a target region of the patient supported on the patient support, wherein respective paths of at least some of the protons of the therapeutic proton beam are deflected in response to contact with the patient, at least one sensor arranged proximal the target region and configured to measure at least one of an impact location of incident protons and an impact energy of incident protons, and a processor in communication with the at least one sensor and configured to calculate at least one of an amount of deflection of the incident protons from the initial path and an incident energy loss from the initial proton energy and to provide an indication of at least one of an electron density within the target region through which the protons pass and an atomic number corresponding to the target region.

In certain embodiments, a method of analyzing accelerated protons in a proton therapy system comprises generating a beam of accelerated protons, directing the proton beam at a target region, arranging one or more sensors adjacent the target region, monitoring at least one of energy and a spatial location of protons incident on the one or more sensors, and calculating one or more of an indication of electron density within the target region and atomic number of the target region. These and other objects and advantages of the invention will become more apparent from the following description taken in conjunction with the accompanying drawings.

Nothing in the foregoing summary or the following detailed description is intended to imply that any particular feature, characteristic, or component of the disclosed devices is essential.

BRIEF DESCRIPTION OF THE DRAWINGS

These and other features will now be described with reference to the drawing summarized below. These drawings and the associated description are provided to illustrate specific embodiments, and not to limit the scope of the scope of protection.

DETAILED DESCRIPTION OF CERTAIN EMBODIMENTS

The present disclosure generally relates to utilizing detected products of certain types of proton-nucleus collision interactions. As described herein, such detected products can be utilized in proton-based therapy and/or imaging systems.

Figure 1:
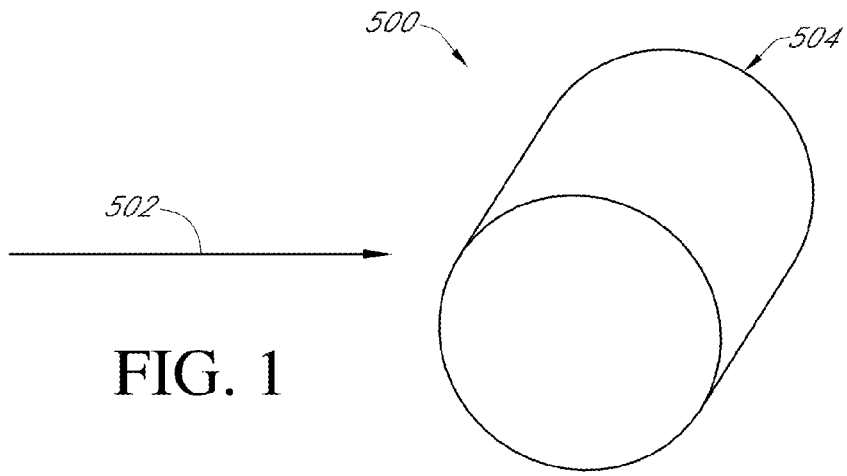
FIG. 1 schematically depicts a proton beam incident on a target volume having materials such as tissue.

FIG. 1 schematically depicts a configuration 500 where a target volume 504 is subjected to a beam of protons 502. The proton beam 502 can be generated and delivered to the target volume 504 in a number of different configurations (e.g., average kinetic energy, average beam width, average number of protons per spill, etc.) by known devices and methods; and thus, further description is not needed herein.

In certain situations, the target volume 504 can be a tissue being characterized. Such a tissue can be part of a human patient. Although many of the examples described herein are in the context of therapy for and/or imaging of human patients, it will be understood that the tissue can also be part of a non-living animal, and the animal (living or not) can include humans as well as non-humans.

Figure 2:
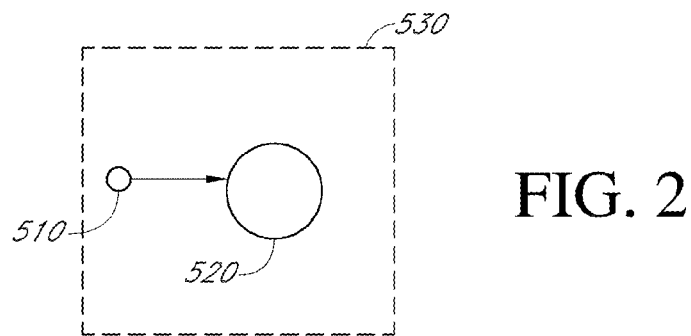
FIG. 2 schematically depicts an example interaction system having a proton interacting with a target nucleus, where the interaction system can arise from the proton beam and target volume configuration of FIG. 1.

FIG. 2 depicts a collision interaction system 530 where a proton 510 (e.g., part of the beam 502 of FIG. 1) collides with a nucleus 520 of an atom in the target volume 504. In certain situations where protons are used for therapy, it can be advantageous to characterize the target volume based on interactions of protons that are same or similar to those of the therapeutic beam. As generally known, use of photon (e.g., X-ray) based imaging techniques such as computed tomography (CT) rely on differences in absorption among, for example, soft tissue and skeletal features. Accordingly, such techniques applied to proton treatment planning is limited by fundamental differences in physical interaction processes—between photons and protons—and therefore can be subject to inherent inaccuracy. For example, X-ray based images typically depict skeletal structures relatively well; but a tumor being treated is not imaged as well or at all.

In the proton-nucleus interaction 530 of FIG. 2, the nucleus 520 can be any one of the nuclei found in the target volume. For example, the nucleus 520 can be that of a commonly found element in tissue, such as carbon, nitrogen and oxygen. Further, the proton's interactions with the nucleus 520 can have impact parameter values ranging from zero (central collision) to those associated with peripheral interactions. The type of nucleus 520, the impact parameter, and energy of the incident proton 510 are some of a number of factors that can influence the type and quantity of products generated from the proton-nucleus interaction of FIG. 2.

Figure 3:
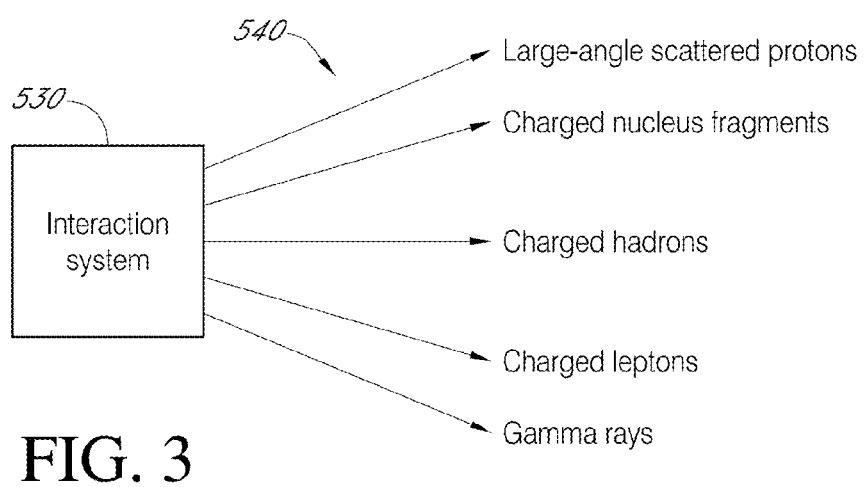
FIG. 3 shows examples of products that can be yielded by the interaction system of FIG. 2.

FIG. 3 shows that the interaction system 530 can yield interaction products 540 such as scattered protons, charged nucleus fragments, charged hadrons such as pions, charged leptons such as electrons and muons, and photons such as gammas. In certain embodiments, one or more configurations of the present disclosure can be configured to detect charged particles in kinematic regions associated with probing of the nucleus by the proton beyond the Coulomb barrier.

For the purpose of description herein, the scattered protons can include protons from the incident beam (primary protons), as well as secondary protons resulting from interactions of the incident proton beam with the target volume. The charged nucleus fragments can include fragments from target nuclei resulting from collisions with the incident protons. The charged hadrons can include pions and kaons; although such hadrons will require that the collision energy be sufficiently high to meet their respective production threshold energies. The charged leptons can include electrons and muons.

Figure 4:
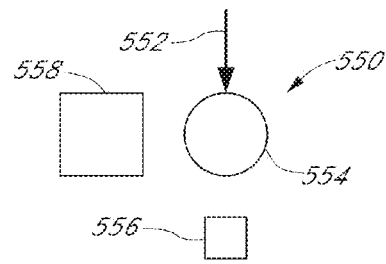
FIG. 4 schematically depicts an example setup configured to detect certain charged particles resulting from interactions of different energy proton beams with a head shaped phantom.

FIGS. 4-9 show examples of simulations and measurements where charged particles are utilized for characterizing interactions of protons with a target volume. FIG. 4 shows an example configuration 550 where a proton beam 552 is provided to a target volume 554 such as a head shaped phantom. A detector 556 downstream of the target volume 554 can be configured to provide functionalities such as triggering and the like in known manners.

In the example configuration 550, a detector assembly 558 is positioned relative to the target volume 554 so as to capture and detect charged particles emitted at or near about 90 degrees (in laboratory frame). The detection and tracking of charged particles can be achieved in a number of known ways. For example, a number of strip detectors (such as Si strip detector) can be arranged appropriately to allow determination of locations of a charged particle at two or more planes, thereby allowing determination of the charged particle's path within the detector assembly. Implementation of various strip detectors, readout of signals, and construction of tracks within the detector assembly can be achieved by known devices and methods.

FIGS. 5 and 6 show graphical representations of a computer simulation of the example configuration of FIG. 4. The computer simulation was facilitated by known GEANT4 simulation software that can be configured and executed in manners known in the art; thus additional details are not necessary for the purpose of description herein. As shown, the head shaped phantom of the measurement setup (550 in FIG. 4) is approximated as an elliptical shaped object.

Figure 5A:
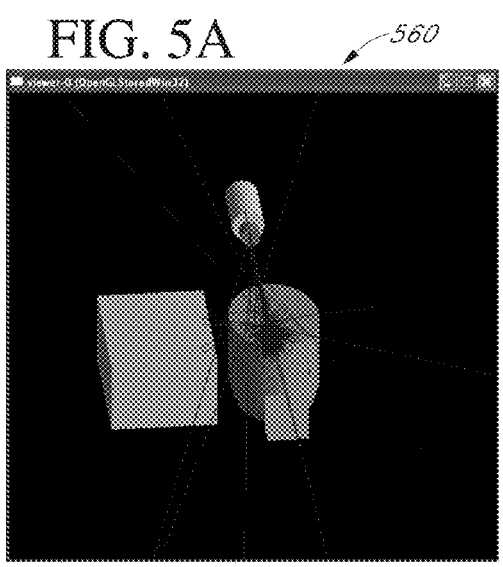
FIG. 5A shows a graphic depiction of proton tracks resulting from computer simulation of interactions of 1,000 protons with kinetic energy of approximately 100 MeV with an approximation of the example setup of FIG. 4.
Figure 5B:
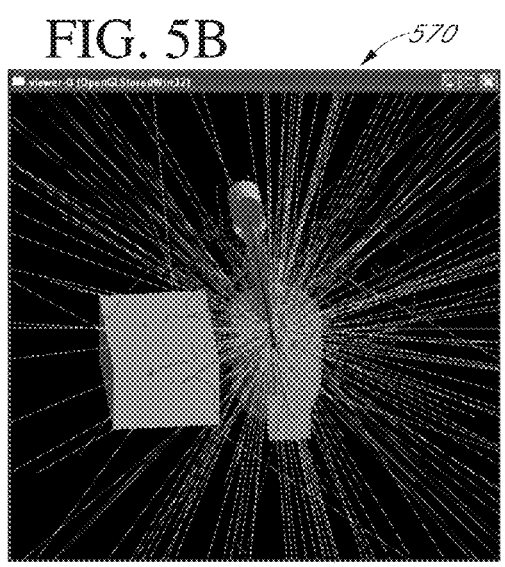
FIG. 5B shows a graphic depiction of substantially all secondary particle tracks (including photons) resulting from the same example configuration of FIG. 5A.

FIG. 5A graphically displays tracks representative of secondary protons resulting from 1,000 interaction events of 100 MeV protons with the target volume. FIG. 5B graphically displays tracks representative of substantially all secondary particles (including photons) resulting from the same events as that of FIG. 5A.

Figure 6A:
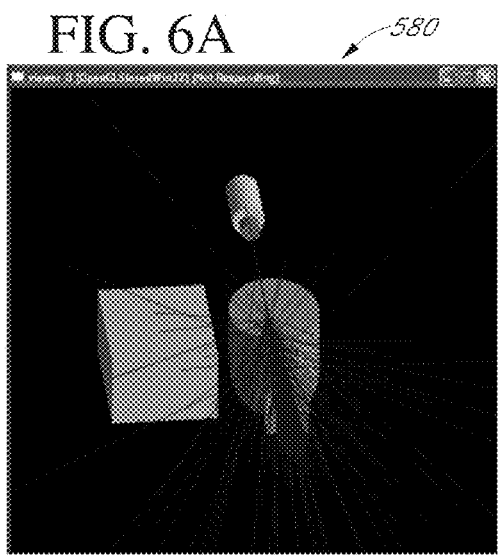
FIG. 6A shows a graphic depiction of proton tracks resulting from computer simulation of interactions of 1,000 protons with kinetic energy of approximately 250 MeV with an approximation of the example setup of FIG. 4.
Figure 6B:
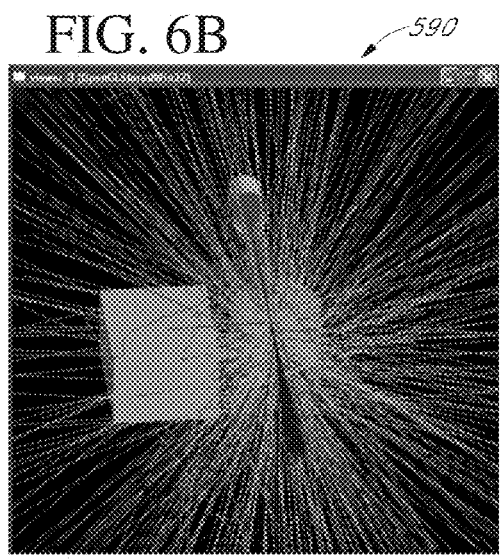
FIG. 6B shows a graphic depiction of substantially all secondary particle tracks (including photons) resulting from the same example configuration of FIG. 6A.

FIG. 6A graphically displays tracks representative of secondary protons resulting from 1,000 interaction events of 250 MeV protons with the target volume. FIG. 6B graphically displays tracks representative of substantially all secondary particles (including photons) resulting from the same events as that of FIG. 6A.

In FIGS. 5 and 6, the non-proton charged particles are essentially electrons. In situations where the beam energy is higher, charged pions can also be produced and detected.

It should be noted that in the simulation depicted in FIGS. 5 and 6, only 1,000 protons are provided for interactions; thus, relatively small numbers of protons are shown to be directed in the acceptance range of the detector. On the other hand, however, even the 1,000 events can provide ample charged particles to the detector. Thus, as described herein, detection of charged particles can provide flexibility in positioning and/or configuring of one or more detectors.

For example, a detector can be configured to detect charged particles without a particle identification capability. Such a detector can be relatively simple, and the relatively high statistics associated with all charged particles can allow use of the detector in low beam intensity situations and/or positioning of the detector at angles (e.g., large angles) where proton density is relatively low.

In another example, a detector can be configured to facilitate particle identification. Specific particles such as protons can be distinguished from other charged particles so as to allow use of protons as target volume characterizing probes. In the simulation example of FIGS. 5 and 6, proton density is relatively low at the detection region. In certain proton therapy situations, however, proton beam intensity can be sufficiently high, such that even one spill of incident protons can provide enough collision events to allow effective characterization of the interactions. Examples of such high beam intensity situations are described herein in greater detail.

Figure 7A:
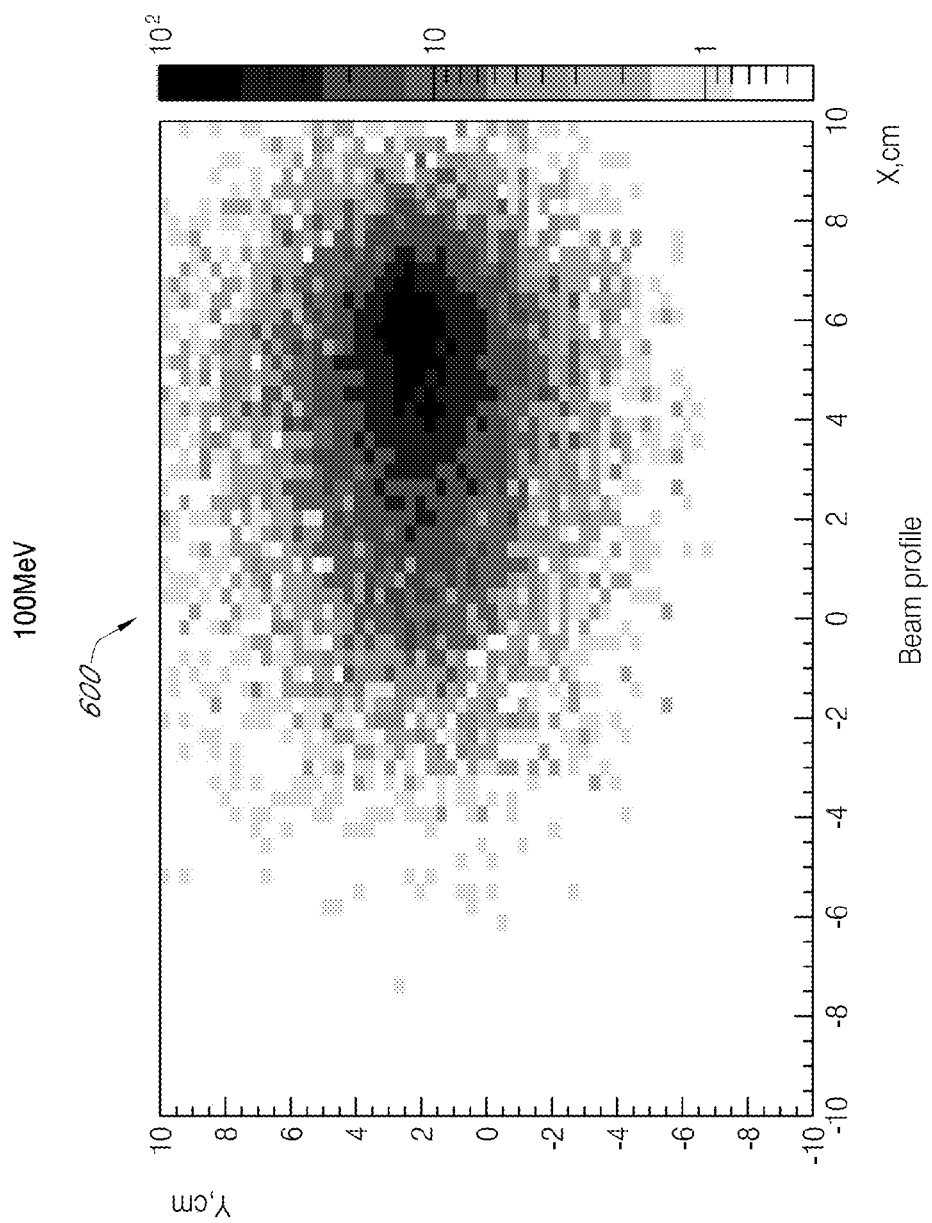
FIG. 7 shows a 100 MeV therapeutic pencil proton beam profile as it passes through the head phantom, where the beam profile is generated based on reconstruction of detected charged particles resulting from the example setup of FIG. 4.
Figures 7B, 7C:
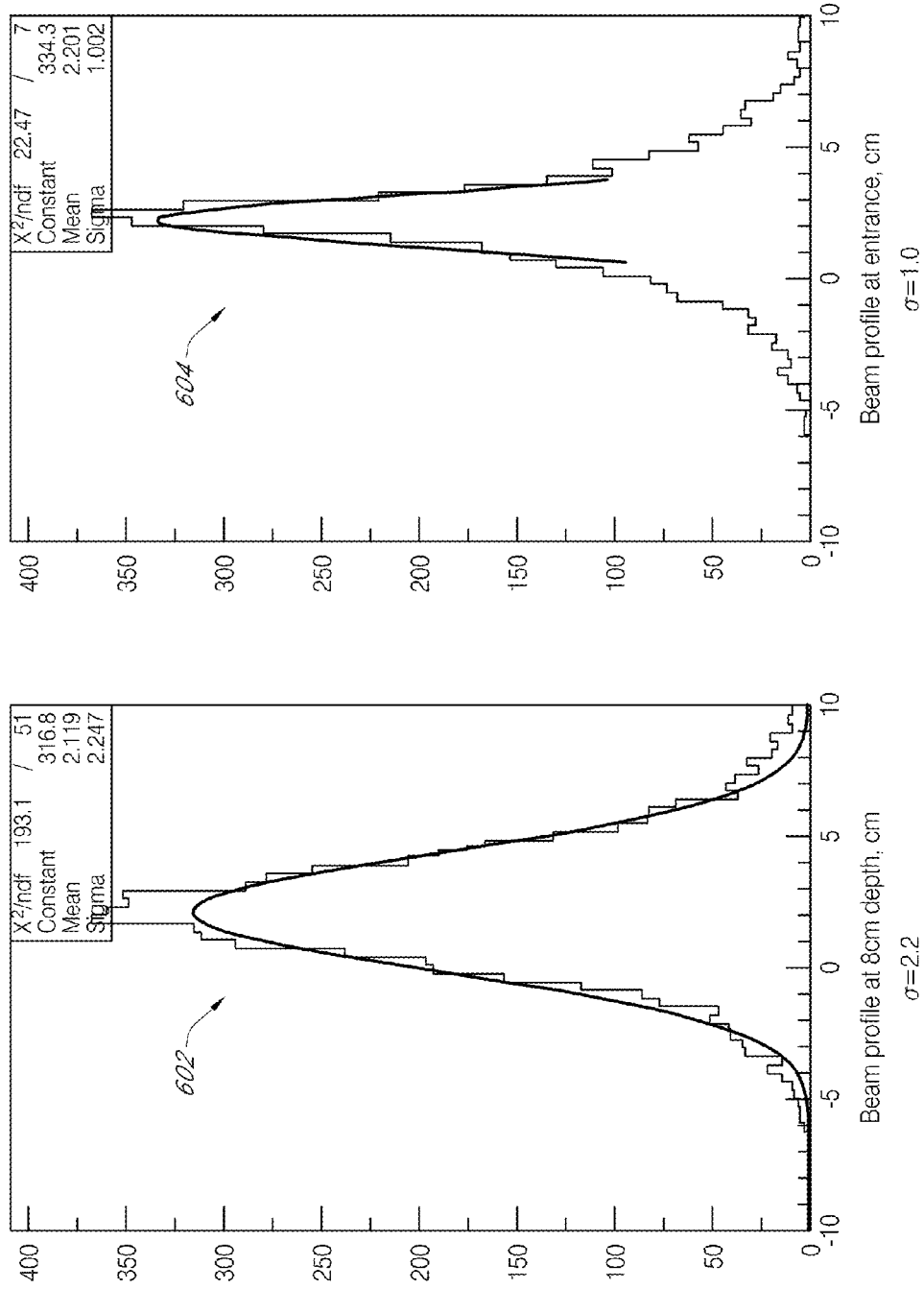
Figure 8A:
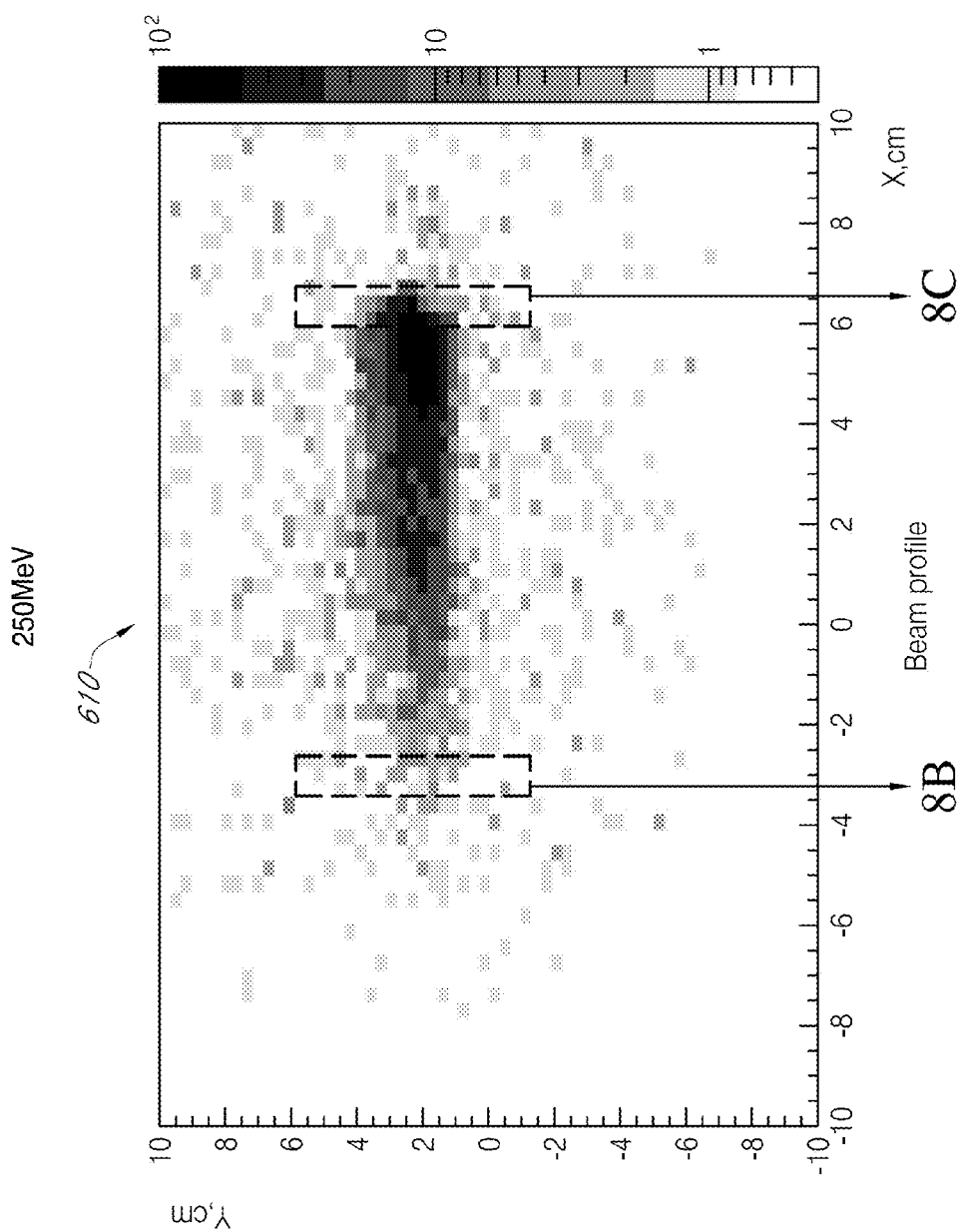
FIG. 8 shows a 250 MeV therapeutic pencil proton beam profile as it passes through the head phantom, where the beam profile is generated based on reconstruction of detected charged particles resulting from the example setup of FIG. 4.
Figure 9A:
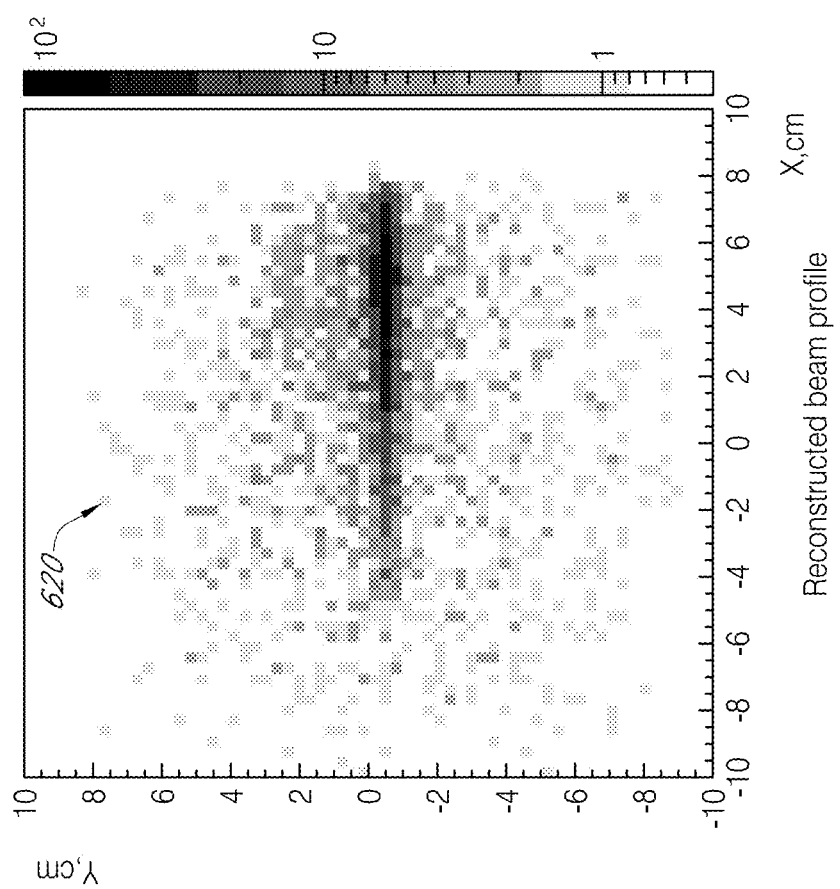
FIG. 9 shows a similar 250 MeV proton beam profile as that of FIG. 8, but where the incident beam is collimated to have a width of about 3.5 mm.
Figure 9C:
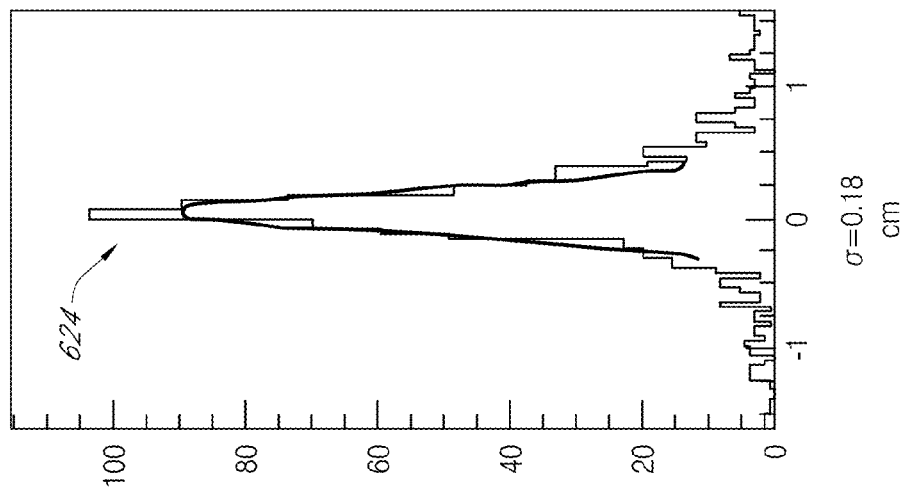
Figure 9B:
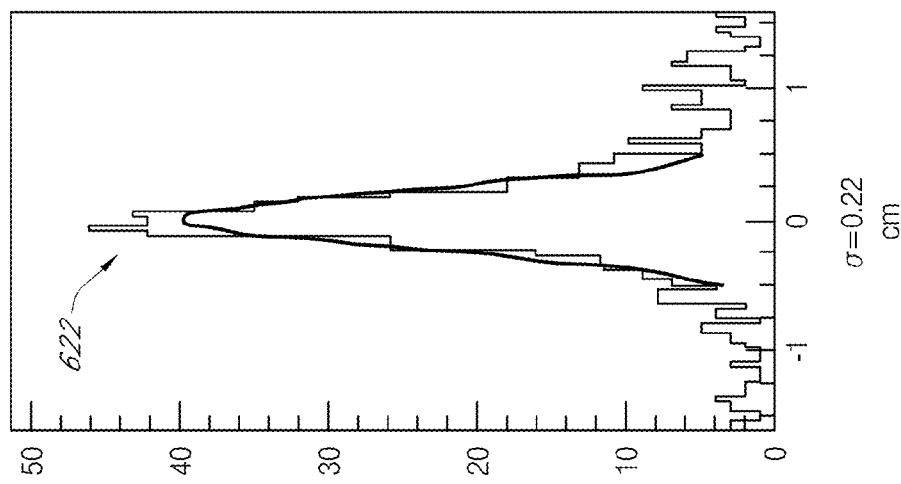

FIGS. 7-9 show measurements of charged particles by the detector 558 of FIG. 4 when the target volume 554 is subjected to different proton beams. For the purpose of description of FIGS. 7-9, the beam travels along the X direction (positive to negative) and generally centered at some Y and Z values.

In FIG. 7, a scatter plot 600 shows an interaction profile (in an XY plane) reconstructed by detected charged particles resulting from a pencil beam of protons having kinetic energy of about 100 MeV. The example pencil beam has an average width of approximately 1 cm and an intensity of approximately $10^8$ protons/spill.

To obtain the scatter plot 600, a track is considered to be valid and due to a charged particle by requiring coincidence of two Si detector sets (each with two perpendicular Si strip orientations) and a Cesium Iodide crystal. Signals from the two Si detector sets provide track candidates, some of which can be validated by requiring deposition of energy (greater than approximately 5 MeV) in the CsI crystal. Track segments validated in the foregoing manner (and representing charged particles) can be projected to an XY plane at a Z value corresponding to the average Z value of the beam, thereby yielding the X and Y values for each of the detected charged particles.

The example 100 MeV beam of FIG. 7 can be representative of a therapeutic proton beam. To obtain data similar to that of the example scatter plot 600, one spill of such a therapeutic proton beam can be used. In the particular example detection configuration yielding the scatter plot 600 of FIG. 7, the detector used had a sensitive area of about 6.4 cm×6.4 cm and a restricted data-taking rate. Because of the detector's restricted data rate, the plot 600 represents data corresponding to few spills. It is estimated that a detector having similar sized sensitive area can allow generation of sufficient data for meaningful analysis with about one spill (of therapeutic proton beam having, for example, about $10^8$ protons per spill) with a higher data-taking rate and/or detector efficiency of about 90% or higher.

As further shown in FIG. 7, example one-dimensional distributions can be obtained at different locations along the beam direction. A distribution 604 is representative of a Y-distribution of charged particles' at the XY plane at an X-slice representative of an entrance portion of the head phantom. A distribution 602 is representative of a Y-distribution of charged particles' at the XY plane at an X-slice representative of a depth of about 8 cm into the head phantom.

As shown, a Gaussian fit of the distribution 604 at the entrance yields a sigma of about 1 cm at the entrance of the phantom head, and at 8 cm depth, the profile widens to about 2.2 cm (sigma in the fit of the distribution 604). It is also noted that the mean Y values obtained from the fits are about 2.2 cm at the entrance and about 2.1 cm at the depth of 8 cm. Such peak location values can provide information about the overall direction of the beam as it traverses and interacts with the target volume.

In FIG. 8, a scatter plot 610 shows an interaction profile similar to that of FIG. 7, but with a pencil beam of protons having kinetic energy of about 250 MeV. The example pencil beam has an average width of approximately 0.8 cm and an intensity of approximately $10^8$ protons/spill.

To obtain the scatter plot 610, track validation and projection to the XY plane are achieved in manners similar to those described above in reference to FIG. 7. Such a beam can be representative of, for example, a proton beam used for radiosurgery applications. Similar to the 100 MeV proton beam example, the particular example detection configuration yielding the scatter plot 610 of FIG. 8 had a restricted data-taking detector with a sensitive area of about 6.4 cm×6.4 cm; thus, the example plot 610 represents data corresponding to few spills. It is estimated that a detector having similar sized sensitive area can allow generation of sufficient data for meaningful analysis with about one spill (of radiosurgery proton beam having, for example, about $10^8$ protons per spill) with a higher data-taking rate and/or detector efficiency of about 90% or higher.

As further shown in FIG. 8, an example Y-distribution 614 is representative of an entrance portion of the head phantom; and an example Y-distribution 612 is representative of a depth at about 10 cm into the head phantom. As shown, the distribution 614 at the entrance yields a sigma of about 0.6 cm at the entrance of the phantom head, and at 10 cm depth, the profile widens to about 0.75 cm. It is also noted that the mean Y values obtained from the fits are about 2.3 cm at the entrance and about 2.1 cm at the depth of 10 cm.

In FIG. 9, a scatter plot 620 shows an interaction profile similar to that of FIG. 8, but with a collimated beam (about 3.5 mm wide) of protons having kinetic energy of about 250 MeV. The example beam is collimated from a beam having an average intensity of approximately $10^8$ protons/spill, and the collimation is estimated to pass through about 30% of such protons to the head phantom.

To obtain the scatter plot 620, track validation and projection to the XY plane are achieved in manners similar to those described above in reference to FIG. 8. The example detector configuration, its restricted data-taking rate, and the detection configuration's capability for one-spill sampling are also similar to those described above in reference to FIG. 8.

As further shown in FIG. 9, an example Y-distribution 624 is representative of an entrance portion of the head phantom; and an example Y-distribution 622 is representative of a depth at about 10 cm into the head phantom. As shown, the distribution 624 at the entrance yields a sigma of about 0.18 cm at the entrance of the phantom head, and at 10 cm depth, the profile widens to about 0.22 cm. It is also noted that mean Y values can be obtained from the fits.

Figure 10:
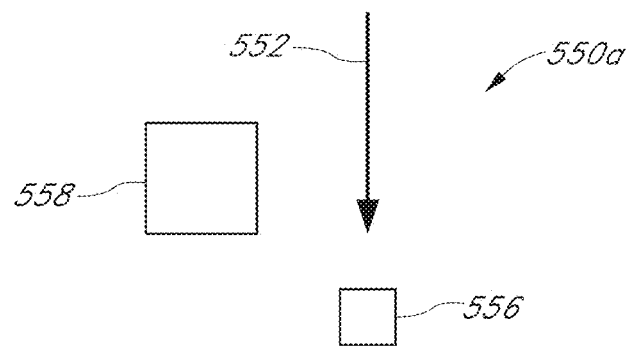
FIG. 10 schematically depicts the example setup of FIG. 4, but without the head phantom.
Figure 11:
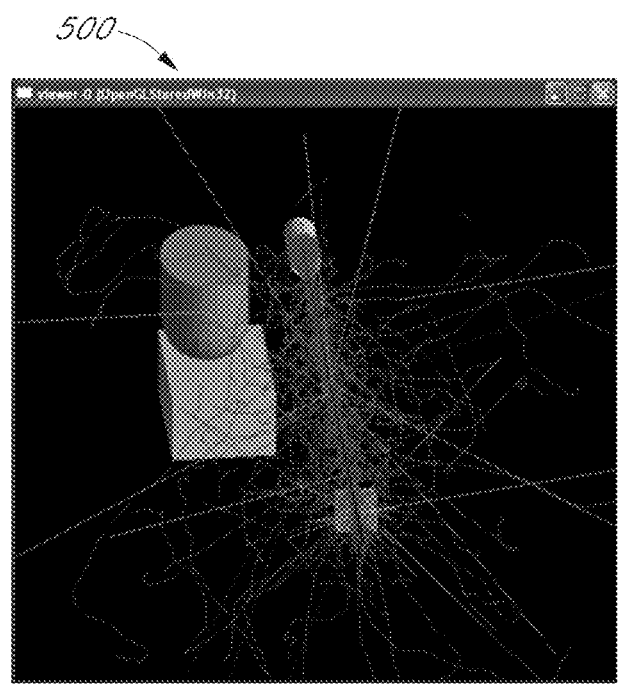
FIG. 11 shows a graphic depiction of secondary particle tracks (including photons) resulting from computer simulation of interactions of 1,000 protons with kinetic energy of approximately 250 MeV with air in the example setup of FIG. 10.
Figure 12A:
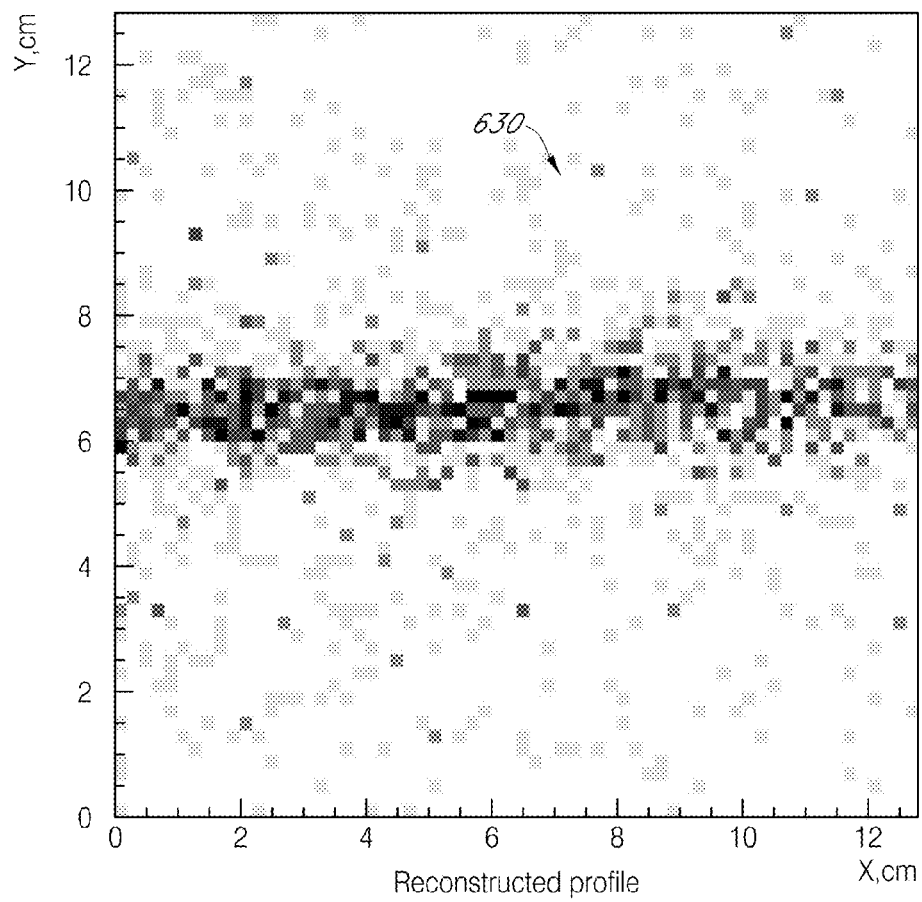
FIG. 12 shows a 250 MeV therapeutic pencil proton beam profile as it passes through the air, where the beam profile is generated based on reconstruction of detected charged particles resulting from the example setup of FIG. 10.
Figure 12B:
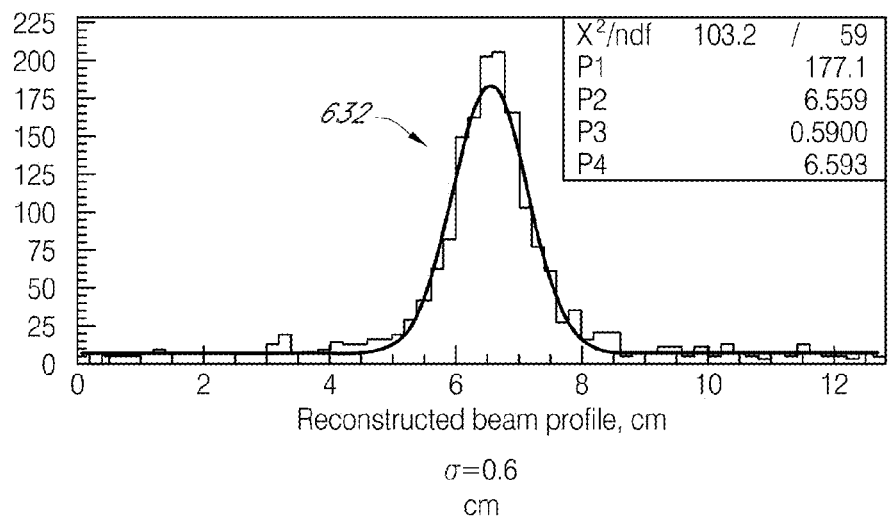

As described above in reference to FIGS. 4-9, detection of charged particles can provide useful information, including information about beam direction and widening of the beam as it traversed the interaction region. FIGS. 10-12 show similar simulation and measurements where the target volume is absent. As is generally known, data obtained in such a manner (sometimes referred to as "target-out" data) can provide useful information about background and systematic effects to be removed from the "target-in" data. In certain situations, however, measurements of target-out data can provide information about the beam itself.

FIG. 10 shows an example configuration 550a that is substantially the same as that of FIG. 4, but with the target volume 554 removed from the beam 552. Thus, after the protons leave a beam pipe or nozzle through a window, they interact with, for example, air. It should be noted that such beam-air interactions also exist between the exit window and the target volume when the target volume is in place.

FIG. 11 graphically displays tracks representative of secondary particles (including photons) resulting from 1,000 interaction events of 100 MeV protons with the air. As shown, numerous charged particles are generated in the beam-air interactions, with the particles being mostly low energy electrons and having relatively short mean pathlengths. There are, however, a significant number of charged particles that are accepted by the detector.

In FIG. 12, a scatter plot 630 shows a beam-air interaction profile that can be obtained in a manner similar to those of FIGS. 7-9. The example detector configuration, its restricted data-taking rate, and sampling of few spills are also similar to those described above in reference to FIGS. 7-9.

As further shown in FIG. 12, an example Y-distribution 632 is representative of a slice of the scatter plot 630 along the beam-air interaction region. The distribution 632 yields a sigma of about 0.6 cm. A number of such distributions can be obtained at different values of X; and from characterization of such distributions, one or more properties of the beam can be obtained. For example, beam divergence in the air and beam direction can be measured and used for purposes such as treatment planning.

Figure 13:
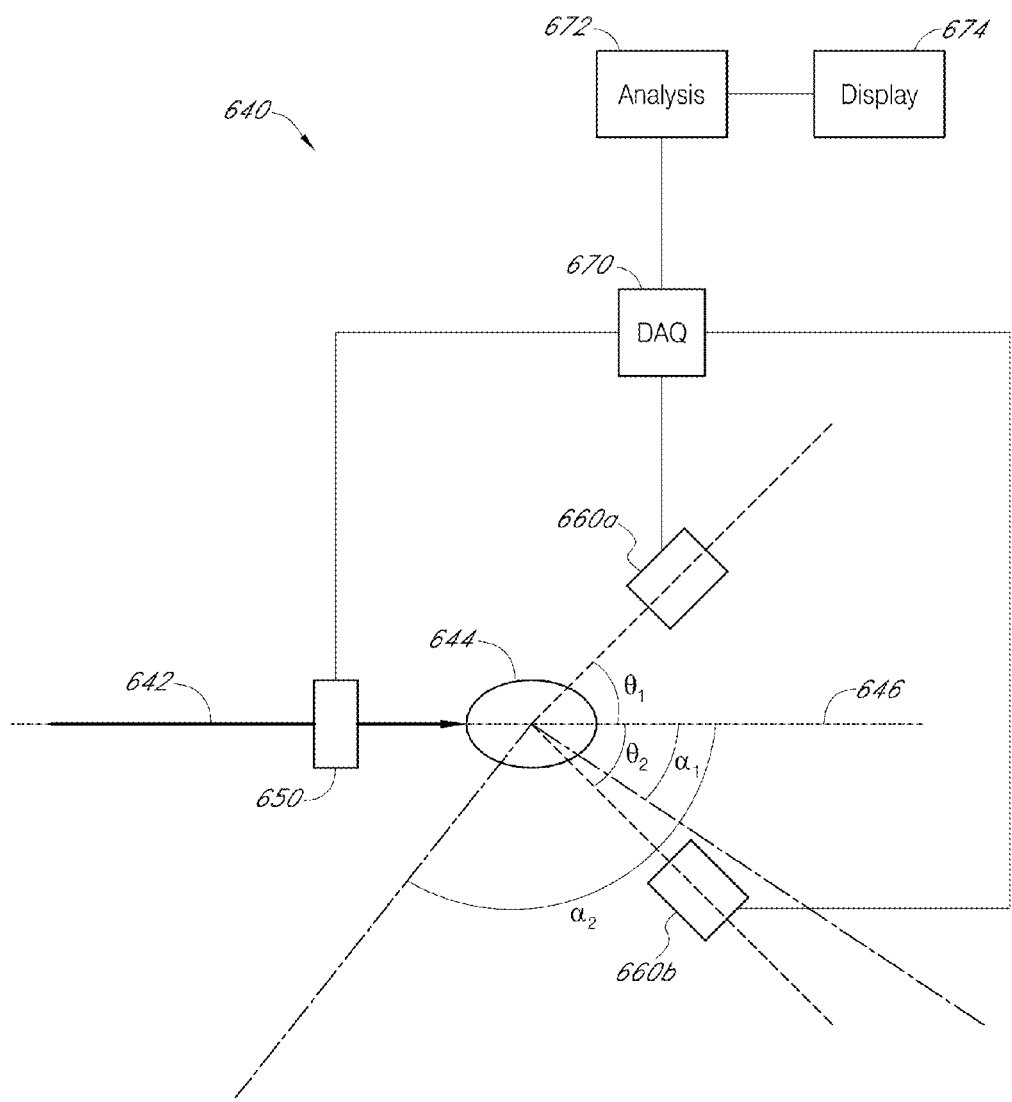
FIG. 13 shows that in certain embodiments, one or more detectors can be positioned relative to the target volume to capture and detect certain types of proton-nucleus interactions.

FIGS. 4-12 generally show how detection of charged particles can be useful for characterizing various proton beam interactions with a target volume. FIG. 13 shows that in certain embodiments, such charged particle detection features can be implemented in a proton beam based system 640. In certain embodiments, the system 640 can be a proton therapy system, an imaging system, or some combination thereof.

The system 640 can include one or more devices (not shown) configured to deliver a beam of protons 642 to a target volume 644. The target volume 644 can be held in place by a support mechanism (not shown in FIG. 13) in known manners.

In FIG. 13, an upstream beam detector 650 can be positioned and configured to allow characterization of the beam 642 prior to entry into the target volume 644. In certain embodiments, a downstream detector (not shown) can also be provided to characterize surviving beam and/or downstream-directed products resulting from the beam-target interactions. Configurations and implementations of one or more of such beam related detectors can be based on known devices and techniques; and thus, further description is not needed for FIG. 13.

FIG. 13 further shows that the system 640 can include one or more detector assemblies 660. In the example shown, two detector assemblies 660a and 660b are provided, with the first detector 660a positioned at an angle of $\theta_1$ relative to a beam axis 646, and the second detector 660b positioned at an angle of $\theta_2$.

It will be understood that the first and second detectors 660a and 660b may or may not be configured the same. Further, the two example detector angles $\theta_1$ and $\theta_2$ may or may not be the same. For example, providing a second detector (660b) may be for the purpose of increasing the number of accepted charged particles from a given kinematic region. In such a situation, and assuming that there is no magnetic field to distinguish charge signs, a second detector substantially identical to the first detector can double the number of accepted particles.

In certain situations, however, it may be desirable to have the two detectors measure different kinematics and/or types of charged particles. In such a situation, the first and second detectors 660a and 660b, and/or the detector angles $\theta_1$ and $\theta_2$, may be configured differently.

FIG. 13 further shows that in certain embodiments, a given detector assembly (e.g., 660b) can be positioned such that its angle ($\theta_2$) is within a selected range (e.g., between angles $\alpha_1$ and $\alpha_2$). Non-limiting examples of how the foregoing detector angles ($\theta$) and angle ranges ($\Delta\alpha$) can be selected are described herein in greater detail.

FIG. 13 further shows that the system 640 can include a data acquisition system 670 in communication with the various detectors (e.g., beam detector 650 and detector assemblies 660a and 660b). Configurations and implementations of such data acquisition system can be based on known devices and techniques; and thus, further description is not needed for FIG. 13.

FIG. 13 further shows that the system 640 can include a data analysis component 672 in communication with the data acquisition system 672. In certain embodiments, the analysis component 672 can receive data from the data acquisition system 672 and generate processed data such as interaction profiles and other quantities described herein.

FIG. 13 further shows that the system 640 can include a display component 674 in communication with the analysis component 672. In certain embodiments, the display component 674 can be configured to facilitate planning of proton therapy based on one or more features as described herein.

Figure 14:
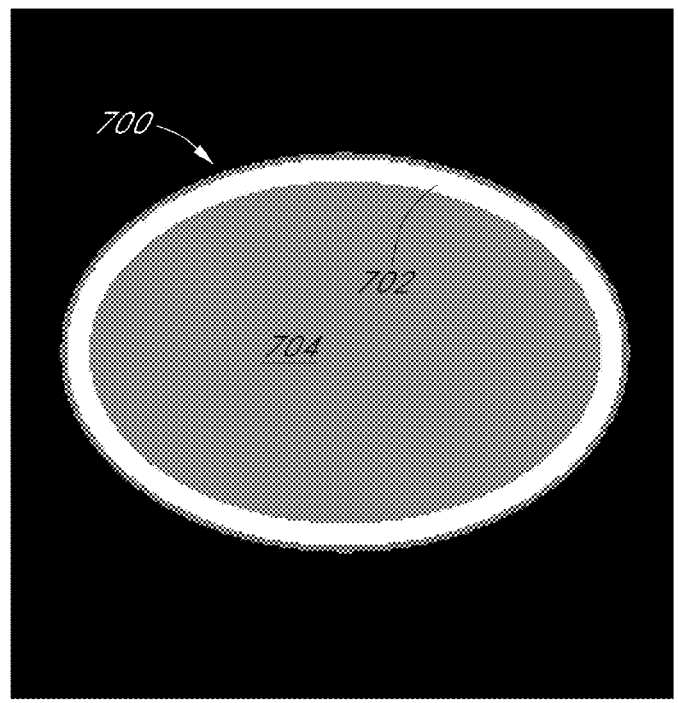
FIG. 14 shows an example phantom object defined in a GEANT4 simulation algorithm, where simulation of proton interaction with the phantom can be utilized to estimate a likely angular distribution of protons and/or other charged particles for determining positioning of the one or more detectors of FIG. 13.
Figure 15:
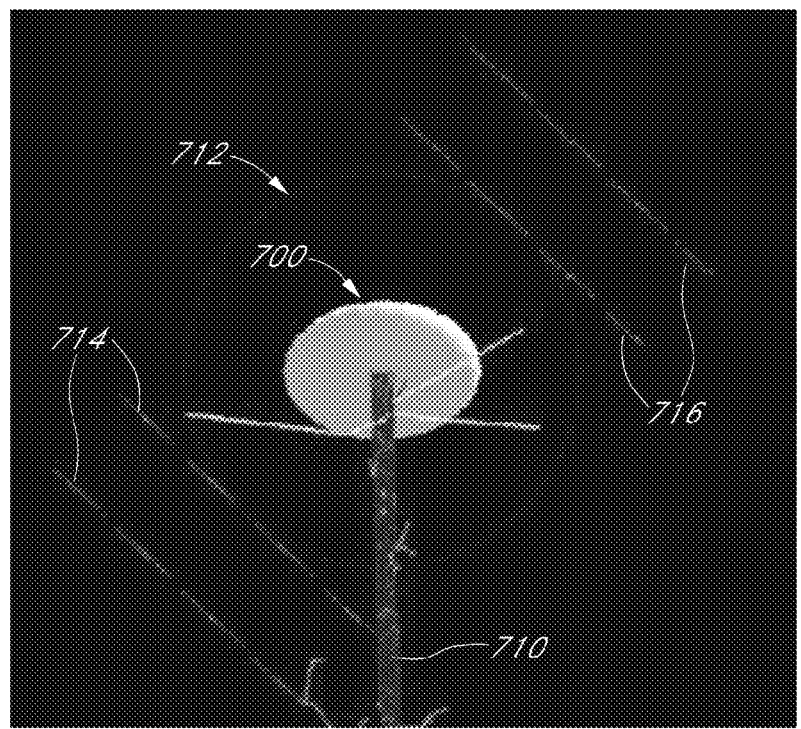
FIG. 15 shows an example sensitive volume that can be defined in the GEANT4 algorithm to facilitate the estimation of the angular distribution of FIG. 14.

FIGS. 14-19 show examples of how one or more detection angles such as angles $\theta_1$ and $\theta_2$ (FIG. 13) can be estimated. In certain embodiments, such estimation can include computer simulation such as that provided by GEANT4 software. FIGS. 14 and 15 depict a target volume 700 defined in GEANT4. Such definition can be user-defined, and in this particular example, can represent a human head having an outer shell 702 approximating a cranial shell and an inner structure 704 approximating a brain material.

In the simulation, a beam of protons 710 can be provided to the target volume 700 as follows. A proton beam 710 that is substantially infinitely thin and having substantially monoenergetic protons can be initiated in a vacuum environment simulating a beam pipe. The beam 710 can be configured to exit the beam pipe through an approximately 25 μm thick titanium window at about 2 m upstream of the center of the head phantom 700. The beam 710 can be positioned to enter the head phantom 700 substantially laterally.

To obtain information about angles of particles being emitted from the head phantom 700, a cylindrical shell 712 shaped sensitive volume (of air) with a radius of approximately 20 cm and a height of approximately 18 cm can be positioned about the phantom 700, such that the centers of the phantom 700 and the sensitive volume 712 are substantially the same. The example height and radius of the sensitive volume 712 approximately represents a distance and acceptance of a detector that can be positioned relative to a head. For example, detector assemblies 714 and 716 are depicted as being positioned at the radius of the sensitive volume 712. It will be understood that such dimensions can vary depending on various therapy and/or imaging systems.

In the simulation, positions and energies of primary protons identified to have undergone a nuclear collision within the phantom 700, and secondary protons, can be recorded by the sensitive shell 712. The simulation was repeated for two incident proton energies, approximately at 100 MeV representative of Bragg peak based treatments and approximately 250 MeV representative of radiosurgery applications.

In FIG. 15 (a screenshot of GEANT4 simulation), 20 primary protons having 100 MeV kinetic energy and resulting interactions are depicted. Both the air sensitive ring 712 and the detectors (714, 716) are shown for illustration; however, only the ring is needed in the simulation to record the capture of various particles from the phantom. Once one or more preferred detection angles are determined, one or more detectors can be positioned accordingly so as to facilitate reconstruction of charged particles' vertices. In FIG. 15, various short-path lines about the beam 710 represent electrons, and the lengthier lines also emerging from the beam 710 and close to the phantom 700 represent gammas.

Figure 16:
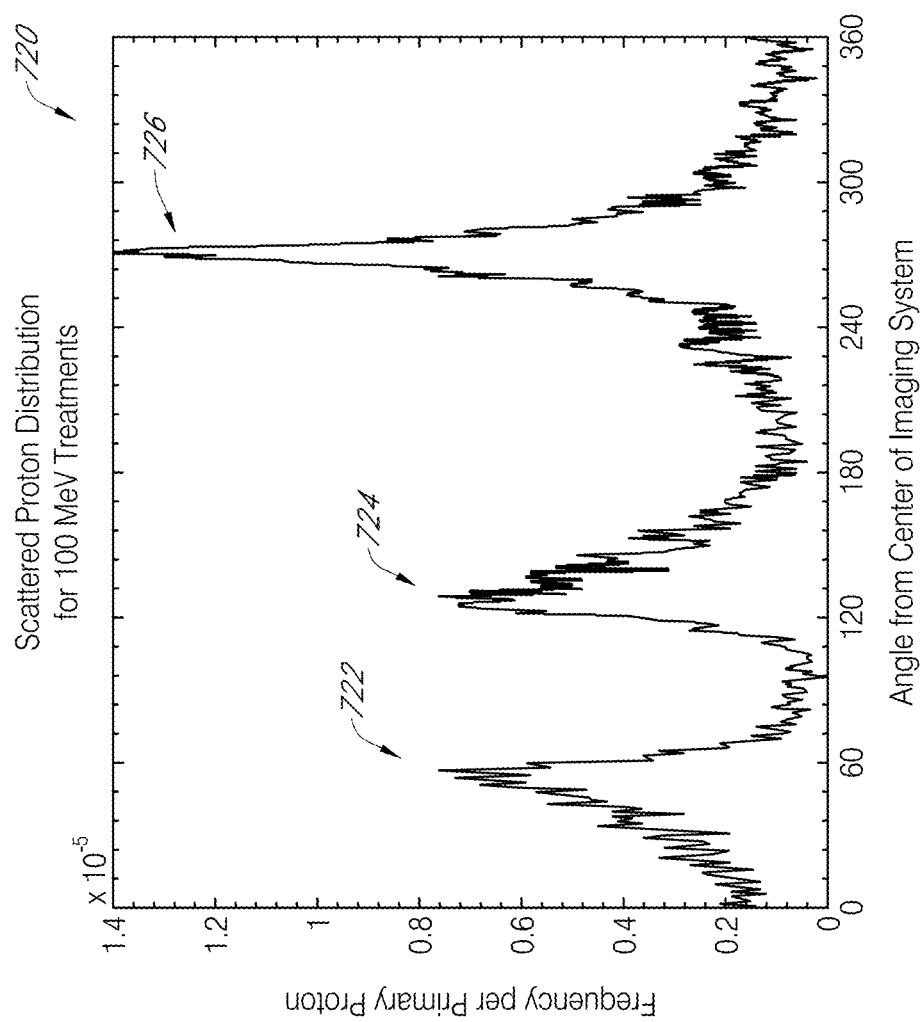
FIG. 16 shows an angular distribution of scattered protons resulting from interaction of 100 MeV protons with the phantom in the simulation configuration of FIG. 15.
Figure 17:
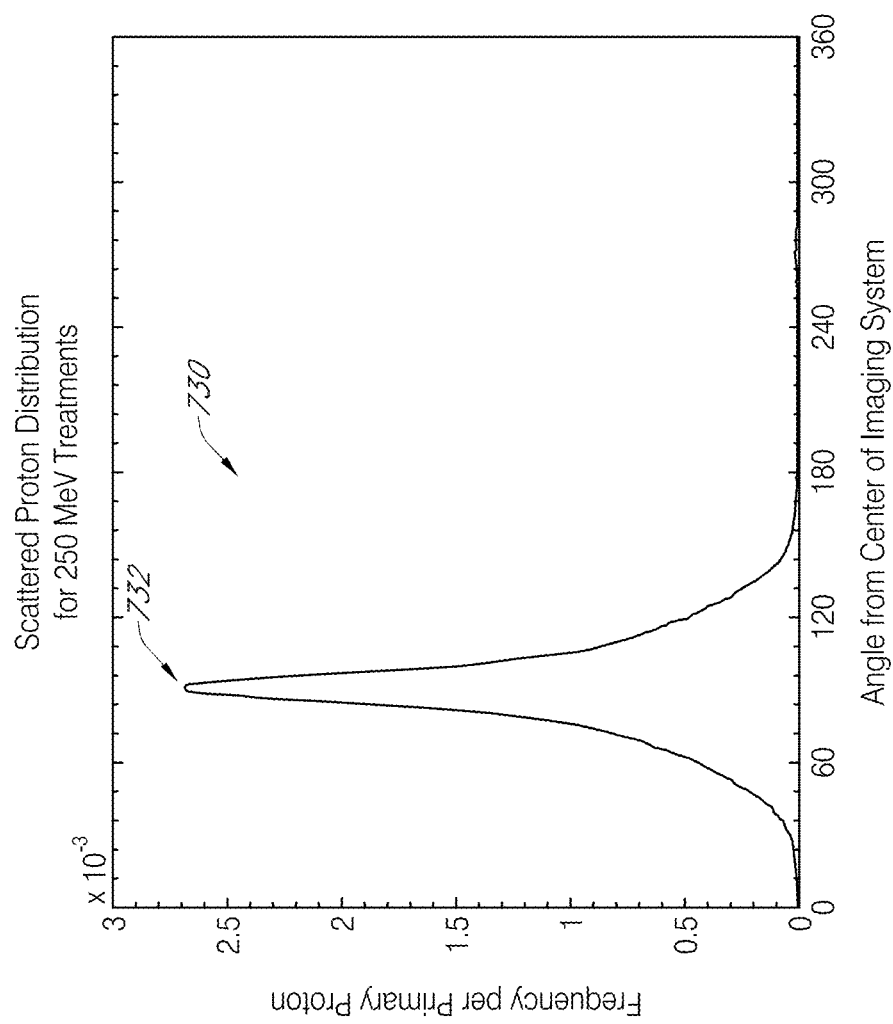
FIG. 17 shows an angular distribution of scattered protons resulting from interaction of 250 MeV protons with the phantom in the simulation configuration of FIG. 15.

Based on the foregoing simulation setup, simulated angular distributions of scattered protons (primary and secondary) are depicted in FIGS. 16 and 17. In FIG. 16, an angular distribution 720 results from interactions of the 100 MeV proton beam with the phantom. In FIG. 17, an angular distribution 730 results from interactions of the 250 MeV proton beam with the phantom. In both configurations, the beam is incident on the phantom at about 270 degrees, and the angles indicated in the distributions (720 and 730) represent emission angles of the protons in the same coordinate system.

In the 100 MeV case, it is noted that a large portion of the scattered protons are backscattered at approximately 270 degrees (peak 726). Less intense secondary peaks (722, 724) at about 55 degrees and 125 degrees are also present. Relative to the beam axis (90 degrees in FIGS. 16 and 17), emission at 270 degrees represent 0 (FIG. 13) of 180 degrees, and emissions at 55 degrees and 125 degrees represent θs of +/−35 degrees.

It is also noted that in FIG. 16, a minimum intensity is present at about 90 degrees. This result is generally consistent with the 100 MeV protons being stopped substantially within the phantom due to the Bragg peak effect.

In the 250 MeV case, the angular distribution 730 yields a single peak (732) at about 90 degrees, indicating that most of the scattered and secondary protons are generally directed along the beam direction. Thus, placement of a detector downstream of the target volume and at or near the beam axis is likely not be desirable, especially in situations (e.g., radiosurgery) where a high intensity beam of protons generally punch through the target volume. At such high intensities, the detector can be saturated and/or damaged from high radiation doses. Similarly, in situations involving high intensity proton beams (whether or not the beam stops in the target volume), it is also not likely desirable to have a detector upstream of the target volume at or near the beam axis, since it will be directly subjected to the high intensity beam.

In certain embodiments, appropriate intensity values acceptable for the detector can be estimated using angular distributions such as those of the foregoing examples. It is estimated that when a beam intensity is about $10^8$ protons per spill, positioning a pair of detectors at about +/−45 degrees relative to the beam axis (45 degrees and 135 degrees in FIGS. 16 and 17) can result in acceptance of particles attributable to interactions on the order of $10^4$ protons (per spill) for the 100 MeV case. For the 250 MeV case, it is estimated that the same positioning can result in acceptance of particles attributable to interactions on the order of $10^5$ protons (per spill).

It is noted that for the example 100 MeV case, the less intense secondary peaks at θs of about +/−35 degrees are about 10 degrees different from the +/−45 degrees referenced in the foregoing estimation. For a detector having a sensitive area of, for example, about 36 cm×18 cm, a 10-degree difference does not affect the particle yield greatly. However, it may be desirable to provide such additional 10 degrees for design reasons. For example, in proton systems where both proton therapy and proton computed tomography (pCT) are implemented, it may be preferable to have a detector used for both therapy and pCT. To achieve such interchangeability, the detector can be positioned downstream of the beam (θ≈0 degree) and the system can be operated with a lower intensity beam suitable for imaging. For therapeutic use, the detector (mounted on, for example, a stiff U-arm) can be rotated to θ of about 45 degrees from the beam axis for beam monitoring, and the system can be operated with a higher intensity beam suitable for therapy.

Figure 18:
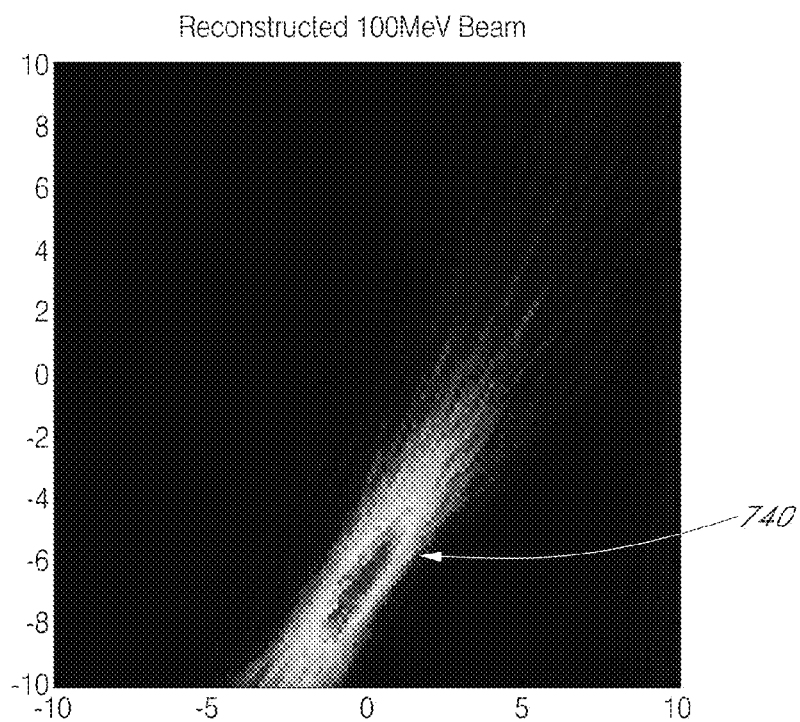
FIG. 18 shows a scatter plot from data for an approximately 100 MeV proton beam profile as it passes through a phantom, where the beam profile is generated based on reconstruction of detected protons with detectors positioned based on the simulated angular distribution of FIG. 16.
Figure 19:
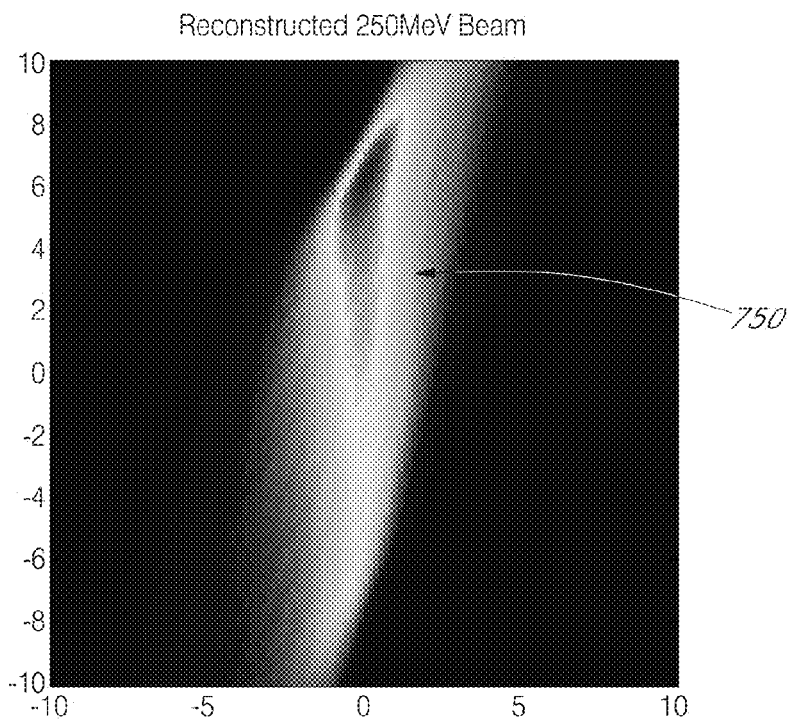
FIG. 19 shows a scatter plot from data for an approximately 250 MeV proton beam profile as it passes through a phantom, where the beam profile is generated based on reconstruction of detected protons with detectors positioned based on the simulated angular distribution of FIG. 17.

Based on the foregoing detector positioning and expected acceptance rate estimates, charged particle detectors placed at about +/−45 degrees (relative to the beam axis) yield measured interaction profiles 740 and 750 depicted in FIGS. 18 and 19 when the phantom is subjected to about $10^8$ primary protons. The example profile 740 represents the 100 MeV beam case; and the example profile 750 represents the 250 MeV case. In both cases, the detected charged particle tracks (producing hits in each of the consecutive Si strip detector planes) were projected back to an image space. The example image space can be set as an approximately 20×20×5 cm$^3$ volume divided into 128×128×25 voxels. The reconstruction was carried out by registering substantially all voxel-ray intersections. In FIGS. 18 and 19, central slices of the image space are shown.

The images in FIGS. 18 and 19 show nuclear scattering probability distributions 740 and 750 (combined elastic and inelastic), and thereby generally define where the primary proton beam travels in the target volume. Note that the X limits of the elliptical shaped head phantom are at about ±10 cm and the Y limits at about ±7 cm. The beam enters the image space from about (0, −10).

As shown in FIG. 18, the reconstructed 100 MeV beam shows the largest number of scattered protons originating from the approximately 0.8 cm thick skull region as the beam enters the phantom. This is to be expected due to the higher effective atomic number of the skull material (relative to that of the brain material). Further, the beam substantially stops at approximately the center of the phantom (0,0).

As shown in FIG. 19, the reconstructed 250 MeV beam shows the largest scattering density in the skull region as the beam exits the phantom. In this example, the vertex of the beam substantially throughout the phantom traversal can clearly be seen. It is noted that the diagonal blurring of the image in FIG. 19 (and also in FIG. 18) is due to the positioning of the detectors at the above-mentioned angles.

The example images of FIGS. 18 and 19 are generated from about $10^8$ primary protons, a number typical for a single treatment beam spill at the Loma Linda University Medical Center.

In certain embodiments, various features of the present disclosure can facilitate planning and/or monitoring of proton therapy. In situations where such proton therapy system can also be used for imaging purposes (e.g., proton CT), one or more of the features described herein can be implemented in a detector for detecting and characterizing passage of imaging protons through the tissue. Further, when the system is switched from imaging mode to therapy mode, the detector can be moved out of the beam direction and be positioned at one or more of the angles as described herein so as to provide the planning and/or monitoring functionalities while avoiding high intensity beams typically associated with therapy.

In certain embodiments, the detector can be positioned so as to accept charged particles emitted from an approximate center of the target region at an angle (relative to the beam direction) in a range of approximately 20 to 90 degrees. In certain embodiments, the angle is in a range of approximately 25 to 70. In certain embodiments, the angle is in a range of approximately 30 to 60. In certain embodiments, the angle is in a range of approximately 35 to 55. In certain embodiments, the angle is in a range of approximately 40 to 50. In certain embodiments, the angle is approximately 45 degrees.

In the context of proton beam therapy, the foregoing estimation of the relative stopping power distributions of protons in a given phantom can facilitate accurate estimation of deposited dose to the phantom. Further, a pre-treatment estimation of the proton's relative stopping power distribution based on, for example, one initial spill of the therapeutic beam, can be facilitated by charged particle detector modules positioned and operated as described herein.

Figure 20A:
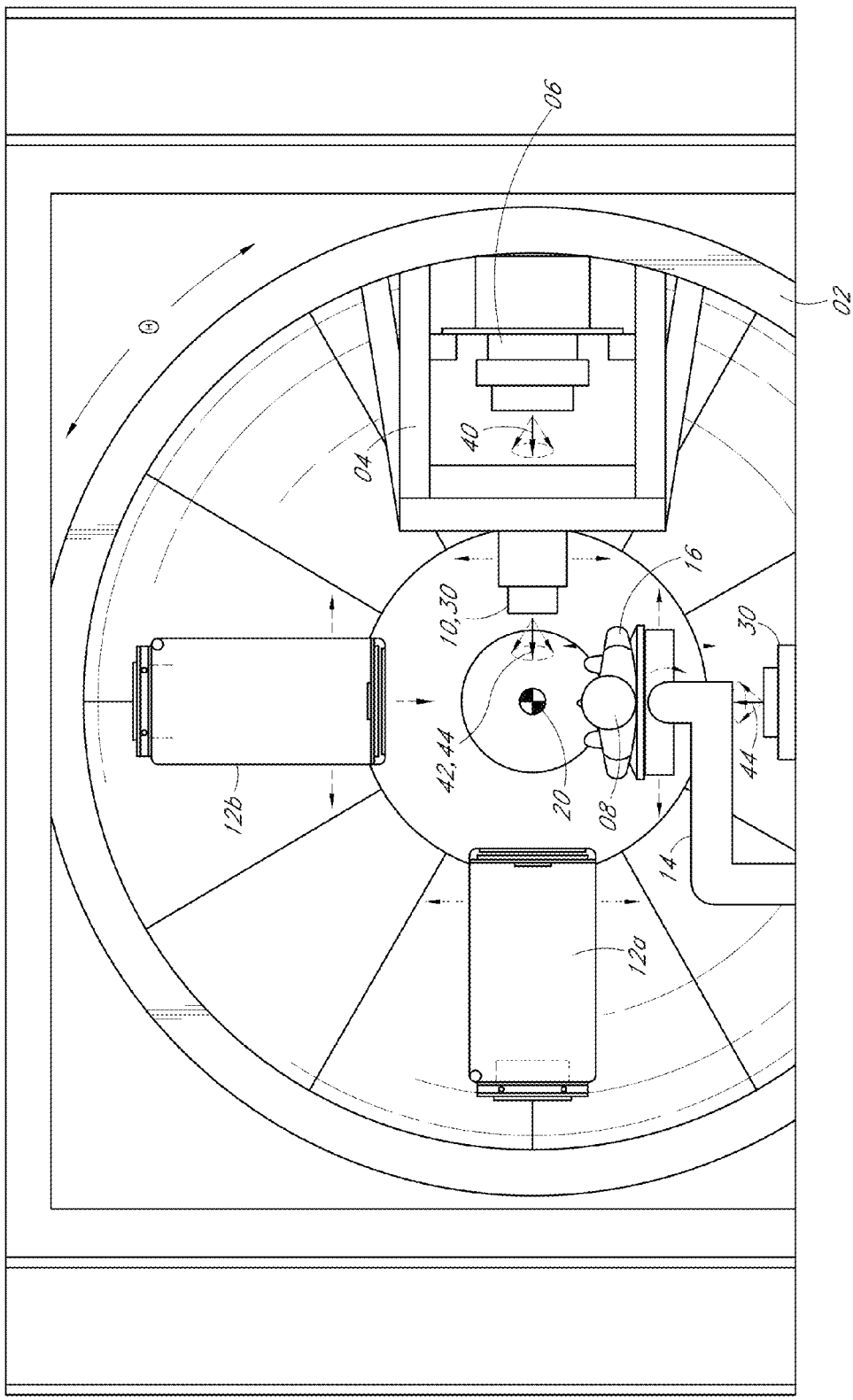
FIGS. 20A and 20B illustrate example configurations of embodiments of a proton radiation therapy system where one or more features of the present disclosure can be implemented.
Figure 20B:
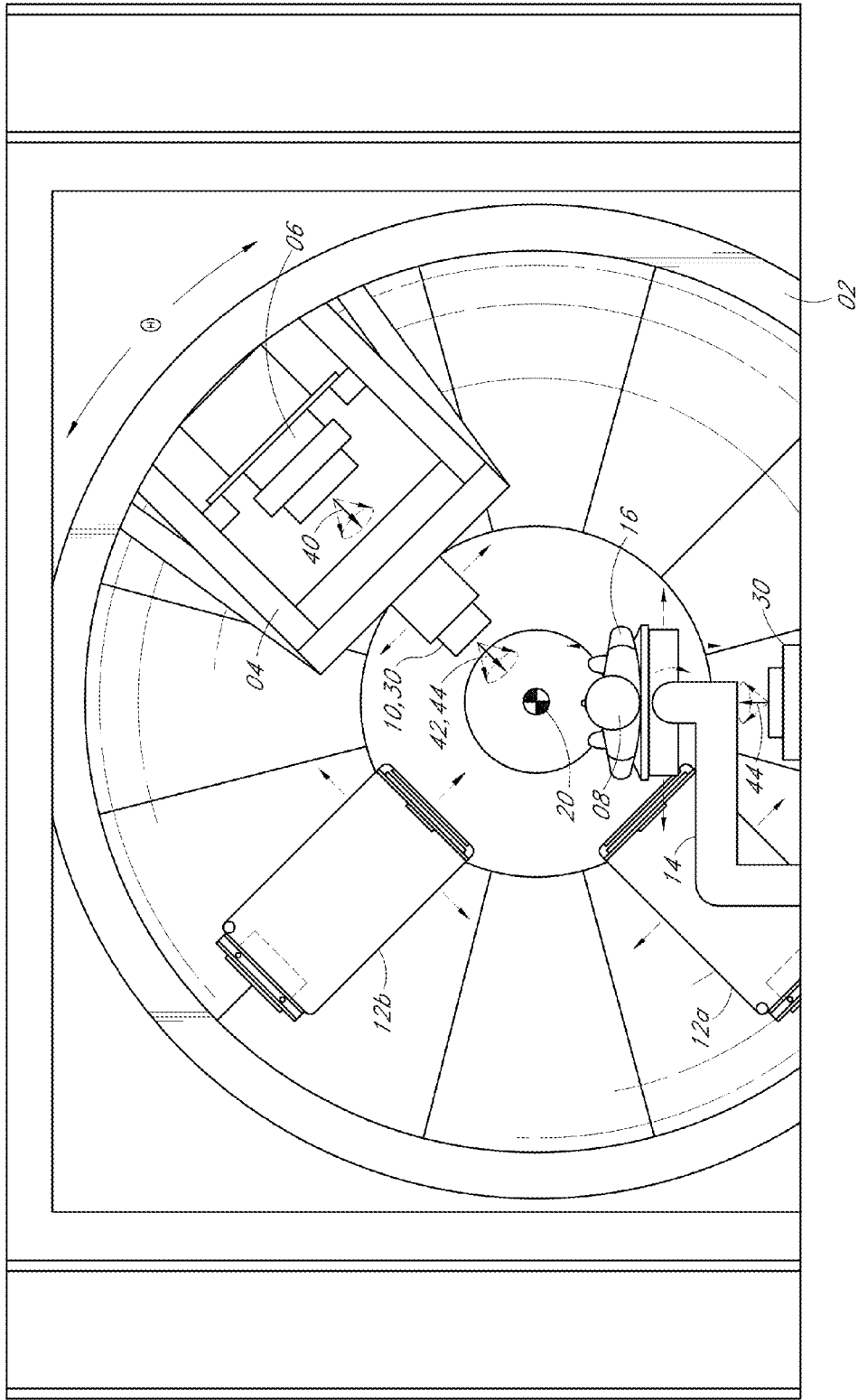

As described herein, one or more features of the present disclosure can be implemented in a proton therapy system and/or a proton-based imaging system such as a proton-CT system. FIGS. 20A and 20B show that in certain embodiments, one or more features of the present disclosure can be implemented in systems such as that found at the Loma Linda University Medical Center.

In FIGS. 20A and 20B, first and second orientations of one embodiment of a particle radiation therapy system are schematically illustrated. Other embodiments of proton therapy systems are described in U.S. Pat. No. 4,870,287 of Sep. 26, 1989, which is incorporated herein in its entirety by reference. The radiation therapy system is designed to deliver therapeutic radiation doses to a target region within a patient 08 for treatment of malignancies or other conditions from one or more angles or orientations with respect to the patient 08. The system includes a gantry 02 which includes a generally hemispherical or frustoconical support frame for attachment and support of other components of the radiation therapy system. Additional details on the structure and operation of embodiments of gantries may be found in U.S. Pat. No. 4,917,344 and U.S. Pat. No. 5,039,057, both of which are incorporated herein in their entirety by reference.

The system also comprises a nozzle 04 which is attached to and supported by the gantry 02 such that the gantry 02 and nozzle 04 may revolve relatively precisely about a gantry isocenter 20. The system also comprises a radiation source 06 delivering a radiation beam along a radiation beam axis 40, such as a beam of accelerated protons. The radiation beam passes through and is shaped by an aperture 10 to define a therapeutic beam delivered along a delivery axis 42. The aperture 10 is positioned on the distal end of the nozzle 04 and the aperture 10 may preferably be specifically configured for a patient's particular prescription of therapeutic radiation therapy. In certain applications, multiple apertures 10 are provided for different treatment fractions.

In the embodiment of FIGS. 20A and 20B, the system also comprises one or more sensors 12a, 12b. In some embodiments, the sensors 12a, 12b can be retractable with respect to the gantry 02 between an extended position and a retracted position. The sensor(s) 12 can comprise "imaging" sensors adapted to detect a location through which a proton and/or x-ray photon passes. The sensor(s) 12 can also, in addition or as an alternative, comprise a calorimeter capability to determine an impact energy of an incident proton. Where provided, a retractable feature of the sensor(s) 12 provides the advantage of withdrawing the sensor(s) 12 from a delivery axis 42 of a radiation source 06 when the sensor(s) 12 is not needed thereby providing additional clearance within the gantry 02 enclosure. In certain embodiments, one or more of the sensors 12, and/or one or more separate sensors, can be positioned and operated according to the present disclosure so as to provide one or more functionalities as described herein.

The system can also comprise one or more x-ray sources 30 which selectively emit appropriate x-ray radiation along one or more x-ray source axes 44 so as to pass through interposed patient tissue to generate a radiographic image of the interposed materials via the sensor(s) 12. The particular energy, dose, duration, and other exposure parameters preferably employed by the x-ray source(s) 30 for imaging and the radiation source 06 for therapy/analysis will vary in different applications.

The system may also comprise a patient positioner 14 and a patient pod 16 which is attached to a distal or working end of the patient positioner 14. The illustrative patient positioner 14 is adapted to, upon receipt of appropriate movement commands, position the patient pod 16 in multiple translational and rotational axes and preferably is capable of positioning the patient pod 16 in three orthogonal translational axes as well as three orthogonal rotational axes so as to provide a full six degree freedom of motion to placement of the patient pod 16.

The patient pod 16 is configured to hold the patient 08 securely in place in the patient pod 16 so to as substantially inhibit any relative movement of the patient 08 with respect to the patient pod 16. In various embodiments, the patient pod 16 comprises expandable foam, bite blocks, and/or fitted facemasks as immobilizing devices and/or materials. The patient pod 16 may also be configured to reduce difficulties encountered when a treatment fraction indicates delivery at an edge or transition region of the patient pod 16.

FIG. 20B shows the same system as FIG. 20A, but with gantry rotation about an angle Θ with respect to the configuration shown in FIG. 20A. The radiation beam axis 40 is still arranged to pass through the gantry isocenter 20. FIGS. 20A and 20B also illustrate an embodiment wherein the sensors 12a, 12b are not opposed symmetrically about the gantry isocenter 20. Rather, in this embodiment, the sensors 12a, 12b are arranged substantially perpendicular or at a 90° orientation with respect to each other. It will also be understand that while FIGS. 20A and 20B illustrate arrangements of two sensors 12a, 12b, this is not a requirement and other numbers and arrangements of sensors 12 are possible.

Figure 21:
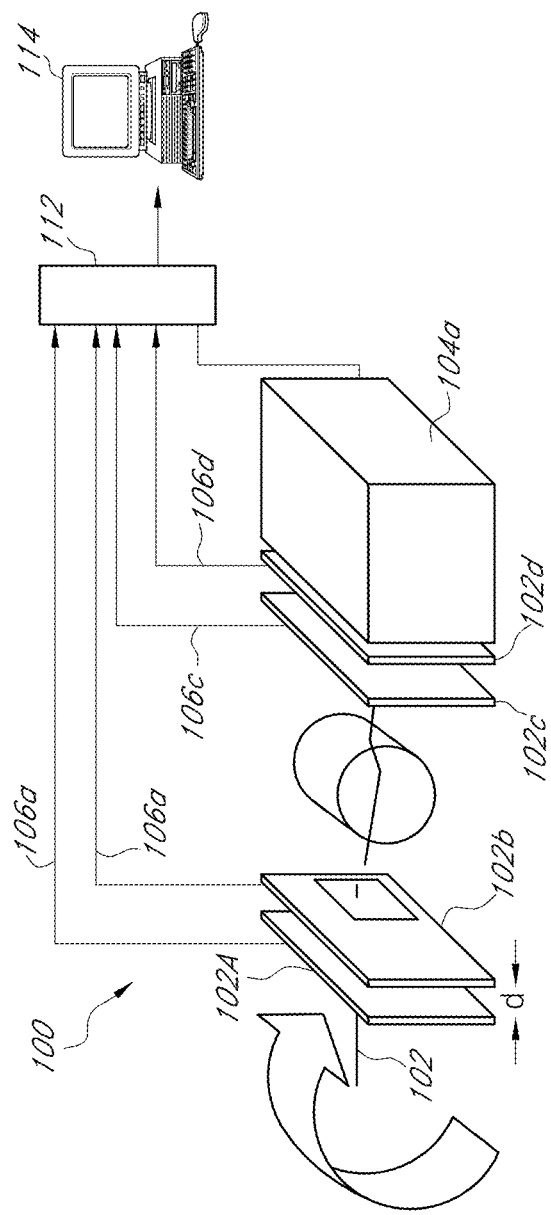
FIG. 21 illustrates a configuration that can be an example of the detection configuration of FIG. 13.

FIG. 21 schematically illustrates embodiments of a proton analysis system 100 referred to hereafter as system 100 for brevity. The system 100 is configured to detect and analyze one or more characteristics of accelerated protons provided by an accelerated proton therapy system, for example as previously described and illustrated with respect to FIGS. 20A and 20B. The system 100 can be further configured to determine, based at least in part on the one or more measured characteristics of the accelerated protons, various characteristics of materials in the path of the accelerated protons, a path of individual or groups of protons and/or characteristics of patient tissue through which the accelerated protons have passed. In certain embodiments, such characterization of the proton beam and/or the tissue can be achieved by configuring and operating the system (e.g., detecting scattered protons, charged particles and/or secondary particles) as described herein.

For example, embodiments of the system 100 are capable of determining an impact energy of an accelerated proton. By knowing an initial energy of the proton as provided by a proton therapy system, the system 100 can determine an energy loss experienced by the proton in traversing the material of interest. This information can be utilized to calculate an estimate of relative electron density and/or atomic numbers of nuclei within a target region.

In some embodiments, the system 100 is capable of estimating a spatial position of impact of an accelerated proton, a secondary proton, and/or other secondary particles. Although mainly in the context of accelerated (primary) protons, some or all of the features described in reference to FIGS. 20-27 can also be applied to secondary protons and other charged particles. In at least some instances, the accelerated proton will have been deflected from an initial path and a determination of the amount or angle of scattering can be utilized to provide indications of the relative atomic number of the material having had deflected the proton.

In some embodiments, determination of relative spatial position of impact of a deflected proton can be used as a data point in calculation of a point of origination of the accelerated proton. With a plurality of such data points provided by a plurality of accelerated proton impacts, the system 100 can computationally reconstruct an original spatial path of the protons thereby providing a direct measurement and confirmation of an actual path of a proton therapy beam that may be deviated from an intended or nominal path.

Such determinations are useful, for example in a treatment planning stage for more accurately implementing a treatment plan by providing empirical measurements of beam path and interaction of the beam with target tissue. For example, some embodiments can more accurately distinguish tissue boundaries and/or provide measurement data indicating a dose delivered to a given target/region. Embodiments can also provide in-process feedback to facilitate more accurate delivery of the planned treatment and determine any indicated adjustments, for example beam direction, initial energy, dose, and the like. In some embodiments, determination and implementation of any indicated adjustments can be performed automatically. In some embodiments, determination and implementation of any indicated adjustments can be performed during a treatment session. These and other advantages and features of embodiments will be more clearly understood with the following detailed description and illustration of features of the system 100.

In some embodiments, the system 100 comprises one or more first sensors 102. In one exemplary non-limiting embodiment, the system 100 comprises a pair of opposed first sensors 102, including sensors 102a, 102b and 102c, 102d. In some embodiments, the first sensors 102 comprise substantially planar silicon strip detectors configured to generate a signal upon impact of an accelerated proton. In other embodiments, the sensors 102 may include any other suitable type of proton detector. In some embodiments, each individual of a pair of associated first sensors 102 are each arranged to be substantially coplanar with the other of the pair of first sensors 102 and to be separated by a distance d from each other. For example, sensors 102a and 102b of FIG. 21 are coplanar and separated by the distance d, and sensors 102c and 102b are coplanar and separated by the distance d. In other embodiments, respective pairs of sensors 102 may be separated by different distances. By providing a pair of substantially coplanar first sensors 102 separated from each other, the system 100 is capable of obtaining two independent but associated data points generated by impact of a given accelerated proton. By obtaining two independent measurements of spatial impact points of a given accelerated proton, the system 100 can employ any of a variety of algorithms to mathematically extrapolate a statistically likely path of a given proton.

In some embodiments, the system 100 comprises one or more second sensors 104. The second sensors 104 (where provided) may be configured to detect an incident accelerated proton and to determine an impact energy thereof. In one embodiment, the second sensors 104 comprised multi-crystal proton calorimeters. It will be understood that some embodiments combine both first sensors 102 and second sensors 104, for example so as to comprise a combined sensor such as the sensors 12a, 12b of FIGS. 20A, 20B. In embodiments where first sensors 102 are provided in combination with second sensors 104, it will generally be preferred that the first sensors 102 be arranged upstream of the second sensors 104, e.g. such that an incident accelerated protons first impact the first sensors 102, pass therethrough, and then impact the second sensors 104.

In order to more accurately monitor the characteristics of the incident accelerated protons, in at least some embodiments it is preferred that the first sensors 102 be capable of tracking an impact location of a proton with a spatial accuracy of better than 100 μm. It is also preferred that the second sensors 104 be capable of determining an impact energy and thus an associated energy loss with a resolution of approximately one percent or less. In other embodiments, however, spatial accuracy of the first sensors may be less than 100 um and the resolution of the energy loss approximated by the second sensors 104 may be greater than one percent.

In some embodiments, one or more of the first and second sensors 102, 104 are substantially fixed in place. In some embodiments, one or more of the first and second sensors 102, 104 can be capable of movement. In some embodiments, one or more first and second sensors 102, 104 are arranged for simultaneous synchronized movement. For example, at least one pair of first sensors 102 and/or an associated second sensor 104 can be coupled for movement for example via the gantry 06 with a radiation source as indicated by the arrow. Thus, the first and/or second sensors 102, 104 can be coupled such that any movement of the radiation source and the corresponding therapeutic proton beam is matched by corresponding movement of the first and/or second sensors 102, 104. These embodiments provide a consistent spatial relative orientation between the first and second sensors 102, 104 and any required movement of the radiation source, for example to provide different treatment fractions to the patient 08.

The system 100 further comprises data connections 106, including data connections 106a, 106b, 106c, 106d, between the first sensors 102 and a data acquisition module 112. The system 100 further comprises data connections 110 between the second sensors 104 and the data acquisition module 112. The data connections 106, 110 in some embodiments comprise wired connections. The data connections 106, 110 can in other embodiments comprise fiber optic cabling. In some embodiments, the data connections 105, 110 can comprise wireless communications. The particular configuration of the data connections 106, 110 is not essential to practicing the described embodiments and the particular implementation can be selected based on the requirements of the particular application.

However, it will generally be preferred that the data connections 106, 110 as well as the associated first and second sensors 102, 104 be capable of relatively high data rates. In some implementations, it is preferred that these components be capable of accommodating data rates of one megabit per second or greater. It will also be generally preferred that these components be hardened against exposure to radiation, such as the accelerated protons and x-ray radiation that is at least intermittently present in a radiation therapy environment. It will also generally be preferred that the components be resistant or have an ability to properly function in an environment having a relatively strong and variable magnetic field, as is also at least intermittently present in a proton radiation therapy setting.

The data acquisition module 112 is configured to receive data signals from the first and second sensors 102, 104 via the respective data connections 106, 110. The data acquisition module 112 can comprise and provide appropriate buffering, amplification, level shifting, multiplexing, synchronization, and similar functions as required for appropriate acquisition and utilization of the data signals provided by the sensors 102, 104.

The system 100 can further comprise a computing device 114 including one or more processors that interfaces with various other components of the system 100 and generates user interfaces for display by an operator, for example. In the embodiment of FIG. 21, the computing device communicates with the data acquisition module 112 and obtains appropriate data or signals corresponding to the measurements obtained by the first and second sensors 102, 104. The computing device 114 can comprise appropriate algorithms, software, firmware, and/or hardware to operate on the data obtained from the data acquisition module 112 and a display to provide indications to a clinician or other user of the observed characteristics of accelerated protons as obtained and provided by the system 100. Additional details of the data manipulation and output provided by the system 100 will be provided below following a further explanation of components and functions of the system 100.

Figure 22:
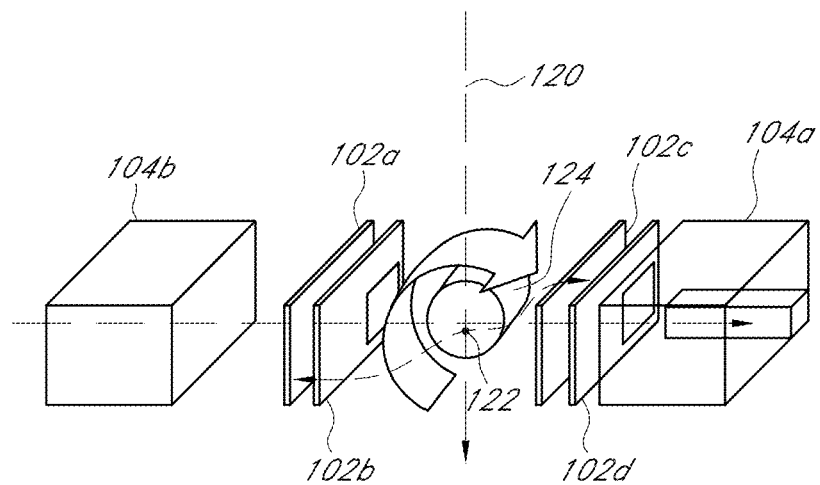
FIG. 22 illustrates another configuration that can be an example of the detection configuration of FIG. 13.

FIG. 22 illustrates an additional embodiment on a configuration of system 100. The embodiment of system 100 illustrated in FIG. 22 is generally similar to the embodiments of system 100 illustrated in FIG. 21 and includes components, such as the data connections 106, 110 and data acquisition module 112, however which are not illustrated in FIG. 22. The embodiments illustrated in FIG. 22 differ by comprising an opposed pair of first sensors 102a, 102b arranged opposite from a pair of first sensors 102c, 102d. The embodiments illustrated in FIG. 22 further comprise a pair of opposed second sensors 104a, 104b. In this embodiments, the opposed pair of first sensors 102a, 102b and 102c, 102d and the opposed second sensors 104a, 104b are arranged opposite and substantially symmetrically on opposite sides of a proton beam 120. The proton beam 120 is directed to pass between the sensors 102b and 102c, but is not arranged to directly impact the sensors. The proton beam 120 is further arranged to align with and pass through a target isocenter 122 in a target region 124. The target region 124 can comprise a wide variety of materials, including inanimate and living tissue. One or more of the opposed pair of first sensors 102a, 102b and 102c, 102d and the opposed second sensors 104a, 104b can be configured for movement as indicated by the arrow. In some embodiments, the opposed pair of first sensors 102a, 102b and 102c, 102d and the opposed second sensors 104a, 104b move substantially in synchrony with each other, for example as coupled to movement of the gantry 02.

As illustrated in FIGS. 20A, 20B, 21, and 22, a radiation source providing the proton beam 120 can be moved, for example rotated, with respect to one or more of the sensors 102, 104. Thus, FIG. 22 for example illustrates that the proton beam 120 can pass between opposed sensors 102, 104 which are arranged substantially symmetrically about the proton beam 120. FIG. 21 in contrast illustrates that a proton beam 120 can be arranged to directly target and pass through first sensors 102a, 102b, 102c, 102d and then impact into a second sensor 104. It will be further understood that a wide variety of orientations and relative positions between the proton beam 120 and the system 100 can be arranged and that the substantially orthogonal (perpendicular or parallel) orientations illustrated in FIGS. 21 and 22 are simply some examples of possible measurement orientations that can be supported by the system 100.

Figure 23A:
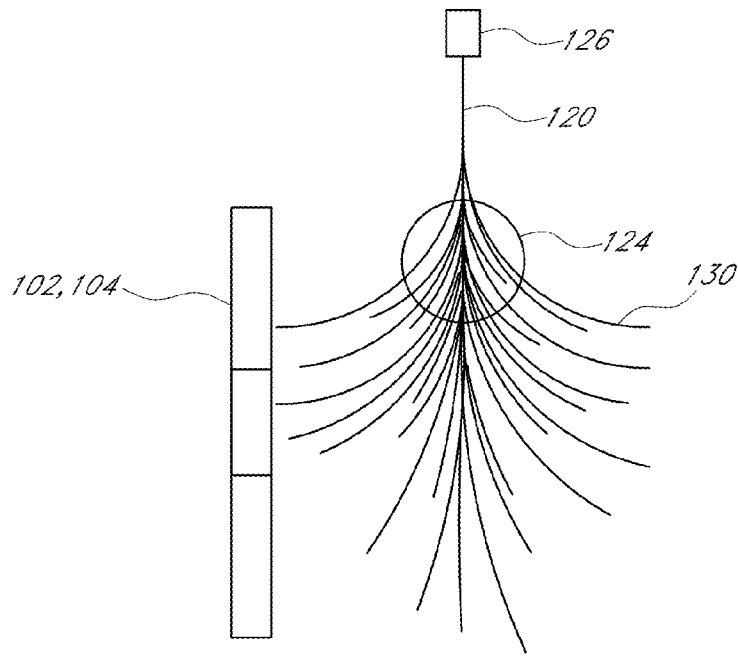
FIGS. 23A and 23B illustrate transverse views of charged particle tracks whose rigidity can be characterized by, for example, application of magnetic field.
Figure 23B:
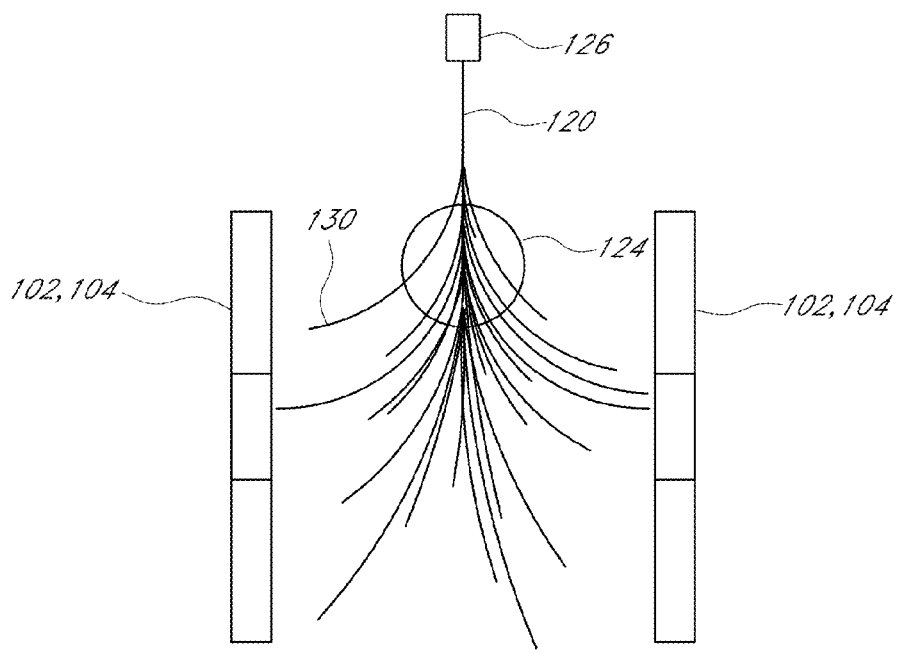

FIGS. 23A and 23B illustrate configurations embodiments of the system 100 comprising first and second sensors 102, 104 arranged on only a single side of a target region 124 (FIG. 23A) and on opposed sides of the target region 124 (FIG. 23B). A proton source 126 provides the proton beam 120 in a relatively tightly focused or pencil beam to intersect the target region 124. FIGS. 23A and 23B illustrate a transverse view or a view generally perpendicular to the proton beam 120. FIGS. 23A and 23B further illustrate views along a direction substantially parallel to the first and second sensors 102, 104. As will be understood, a wide variety of energies and doses of the proton beam 120 can be provided depending on the needs of a particular application. With selection of a high enough energy of the protons, the proton beam 120 can be configured to substantially pass through the target region 124. Selection of a more moderate energy of the proton beam 120 can result in a measurable proportion of the proton beam 120 deflecting from the target region 124 and impacting the sensors 102, 104. Such interactions can yield a number of charged particles (indicated as 130). In certain embodiments where magnetic field is applied to differentiate positive and negative charged particles, providing two detectors (FIG. 23B) can facilitate separation and identification of differently charged particles emerging from the target region 124. By analyzing the characteristics of the deflected protons and/or other charged particles, for example the relative spatial position of the deflected protons 130 and/or their remaining energy, the system 100 can provide valuable indications of the characteristics of the target region 124 and the proton beam 120.

Figure 24:
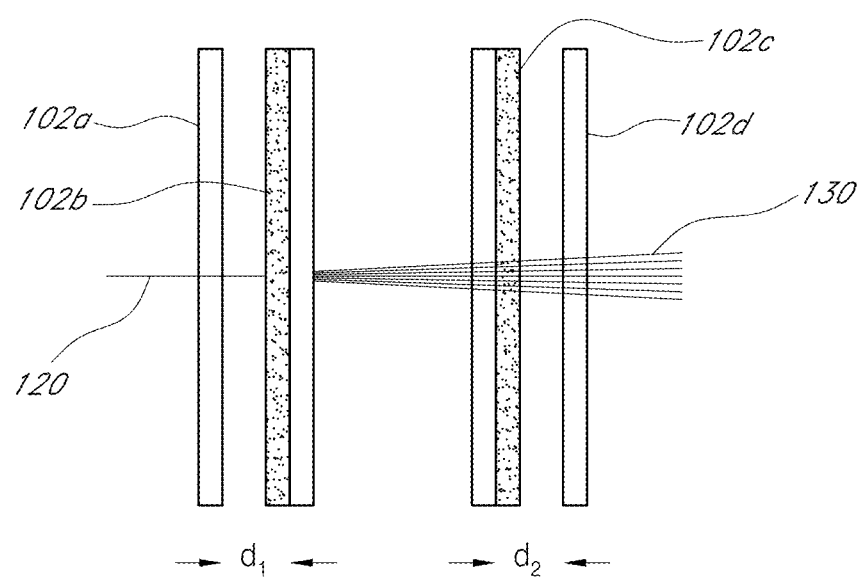
FIG. 24 illustrates a side section view of an incident proton beam and embodiments of protons sensors and illustrating divergence of the incident proton beam.

FIG. 24 illustrates schematically in side section view a further configuration of the system 100. As can be seen, the proton beam 120 follows an initial path and is arranged to intersect a first pair of first sensors 102a, 102b substantially perpendicular to a major plane of the first sensors 102a, 102b. The first sensors 102a and 102b are arranged to be substantially parallel with each other and to have a spacing $d_1$ therebetween as previously described. The first sensors 102c and 102d are arranged to be substantially parallel with each other and to have a spacing $d_2$. The distances $d_1$ and $d_2$ can be substantially the same or can differ. The proton beam 120 substantially passes through the first sensors 102a, 102b and impacts a second pair of first sensors 102c, 102d. However, for at least certain mean proton energies, the deflected protons 130 define at a least a degree of divergence of individual protons from the initial path of the proton beam 120.

Figure 25:
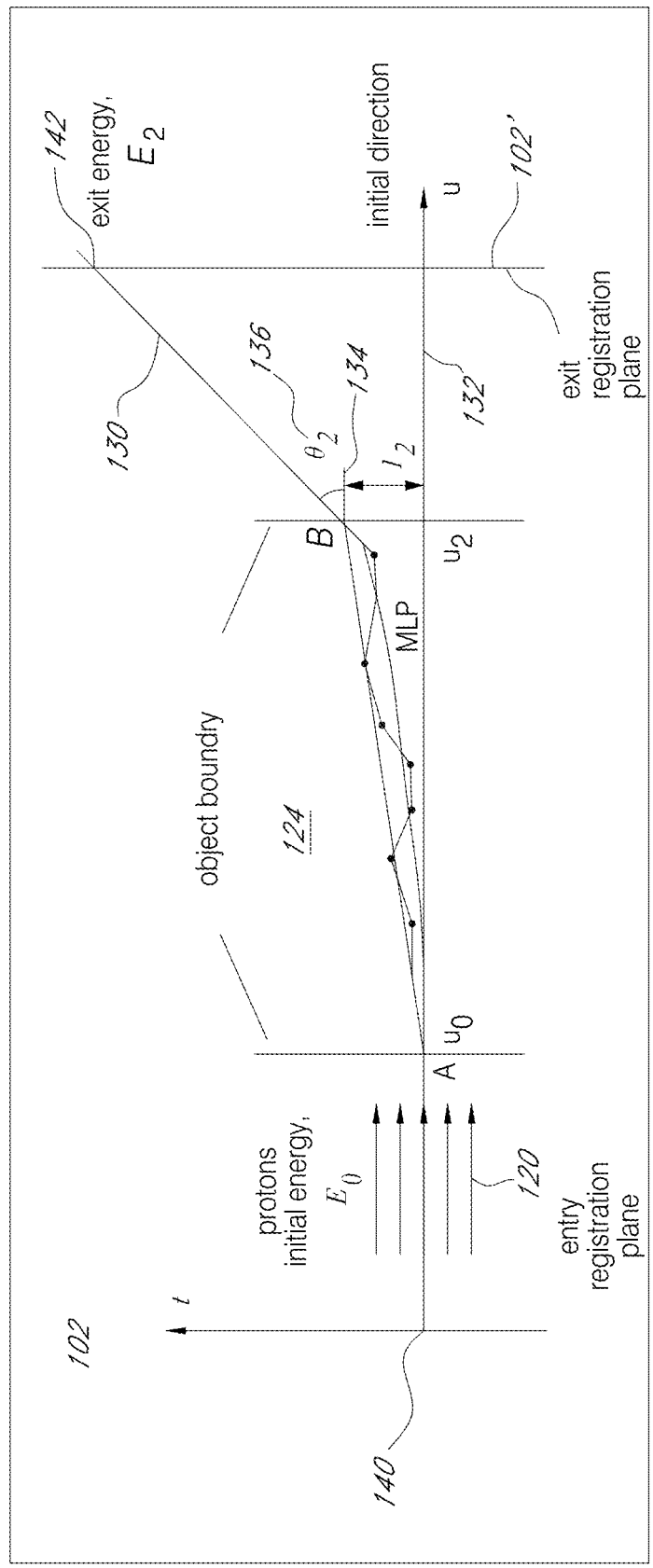
FIG. 25 is a schematic illustration of an exemplary deflected incident proton and various characteristics thereof as measured by embodiments of a proton scattering analysis system.

FIG. 25 is a graph illustrating an exemplary divergence of the deflected protons due to, for example, multiple Coulomb scattering. As illustrated in FIG. 25, the individual protons of the proton beam 120 have an initial energy indicated $E_0$. While the proton beam 120 in at least certain implementations preferably comprises a relatively tightly focused beam, the proton beam 120 will in practice have a non-zero width as schematically indicated by the vertical spacing of the individual rays of the proton beam 120. The individual protons of the proton beam 120 impact the target region 124 at a first object boundary indicated as $u_0$ and leave the target region 124 at a second object boundary indicated $u_2$. A path of an individual proton is illustrated schematically to describe a plurality of deflections within the target region 124. The sum result of these individual plurality of deflections can result in a given proton diverging from an initial or nominal path indicated by the horizontal straight line and indicated with the designator 132. This deflection from the initial or nominal path 132 can comprise one or both of an off-axis translation indicated by the designator 134 by a distance indicated $t_2$ and/or by a deflection angle 136 indicated also by the angle $\Theta_2$.

Information about the path and energy of a given proton can be obtained and considered based on observations regarding the proton as the proton passes through a first sensor pair of sensors (e.g., 102a, 102b), where the pair of sensors comprise an entry registration plane 140, for example. The entry registration data provides initial information regarding the proton, for example including an initial or nominal path vector 132 and an initial energy $E_0$. An exit registration plane 142, for example comprising a second pair of sensors (e.g., 102c, 102d), provides corresponding exit registration data including any deflection angle 136 and off axis translation 134 and exit energy indicated $E_2$.

Energy loss experienced by a proton traversing the target region 124 corresponds to relative electron density $\eta_e$ along the path followed by the proton. Thus, an energy loss integral between the exit energy $E_2$ and the initial energy $E_0$ corresponds to a path integral of electron density within the target region 124 along that path. By analyzing a plurality of such energy losses by individual protons, the system 100 provides a clinician valuable information about the internal characteristics of the target region 124 without directly physically accessing the target region 124. The energy loss can be represented by the following equations.

$$\frac{dE}{du} = F(E)\eta_e(u)$$

$$\int_{E_2}^{E_0} \frac{1}{F(E)} dE = \int_L \eta_e(u)\,du$$

In a similar manner, the variance of the scattering angle of the deflected protons 130 is indicative of a relative atomic number $z$ of the target region 124. The relationship between scattering angle and atomic number can be represented by the following equations.

$$\frac{d\sigma_\theta^2}{du} = G(p(u), \beta(u))\xi_z(u)$$

$$\int_0^{\sigma_\theta^2} d\sigma_\theta^2 = \int_L G(p(u)\xi_z(u))\,du$$

As previously described and illustrated with respect to FIG. 23, deflected protons 130 from a proton beam 120 that is not directed to intercept first and second sensors 102, 104 can nonetheless be at least partially detected by the first and/or second sensors 102, 104. While protons have a non-straight statistical path, information about the spatial location of impacts of the deflected protons 130 can be analyzed to determine a spatial location of the initial path of the proton beam 120.

Each individual proton detected can provide independent information about itself and a target region 124. As the history of a given proton is inherently discreet, some embodiments employ discreet approaches in analyzing and utilizing data obtained from the protons. The target region 124 can be conceptualized as a black box object comprising a three dimensional spatial distribution of target parameters x that can produce corresponding measured data y. Recovery of the target parameters x under an object function F from the measured data y requires inversion of the operator F.

$$Fx=y \text{ solve}\Rightarrow x=F^{-1}y$$

A discreet linear problem approach requires that the target parameter and measured data both be vectors and the operator F be a matrix.

A variety of discreet approaches in analyzing the measured data, for example spatial positions through which the protons pass and/or initial and subsequent proton energies, are possible including a filtered back projection (FBP) as well as algebraic reconstruction techniques (ART). In at least certain implementations, utilization of a most likely path (MLP) in combination with an algebraic reconstruction technique can provide improved spatial resolution.

As previously noted, a variety of algorithms and approaches can be utilized in analyzing the data measurements obtained by the system 100. Each algorithm or approach can have individual advantages and disadvantages and the selection of an appropriate algorithm can depend on a variety of factors including but not limited to available processing capability, speed requirements, resolution/accuracy requirements, and the like.

Exemplary algorithms can include a fully sequential algebraic reconstruction technique (ART) such as Kaczmarz algorithms as used for example in computed tomography. The fully sequential ART is a standard approach and has been used in numerous previous applications. Fully sequential ART is known to work in proton computed tomography. However, a fully sequential ART algorithm can be slow due to its sequential nature. In principal, a fully sequential ART can be modified for parallel operation.

A fully simultaneous approach, (e.g. Cimmino 1937) converges to a least squares minimum, however is typically relatively slow due to small weight factors (1/m). A block iterative projection (BIP) (Aharoni and Censor 1989) provides simultaneous projection within blocks of hyper planes. The sequential projection of blocks iterates with weighting according to block size. This avoids the drawbacks of a small 1/m. A string averaging algorithm (Censor, Elfving, and Herman 2001) utilizes sequential projection within strings of hyper planes and operates in parallel within all strings. A convex combination of all strings iterates. Component averaging (CAV) (Censor, Gordon, and Gordon 2001) is fully simultaneous similarly to Cimmino's algorithm of 1937. CAV replaces 1/M weighting factor by a family of diagonal matrices with diagonal elements equal to number of protons intersecting a jth voxel. CAV leads to nonorthogonal projections and can be made block iterative (BICAV). A diagonally relaxed orthogonal projection (DROP) (Censor, Herman, Elfving, Touraj 2008) is also fully simultaneous like CAV and Cimmino's algorithm. DROP employs component average weighting as in CAV, but with orthogonal projection. DROP can also be made block iterative (BIDROP).

As such projection or reconstruction algorithms are highly computationally intensive, particularly considering the large amounts of data points involved, hardware acceleration of the processing is generally advantageous. General purpose graphics processing units provide useful advantages in accelerating the computational processes and are also widely available and relatively inexpensive to purchase and use.

Figure 26:
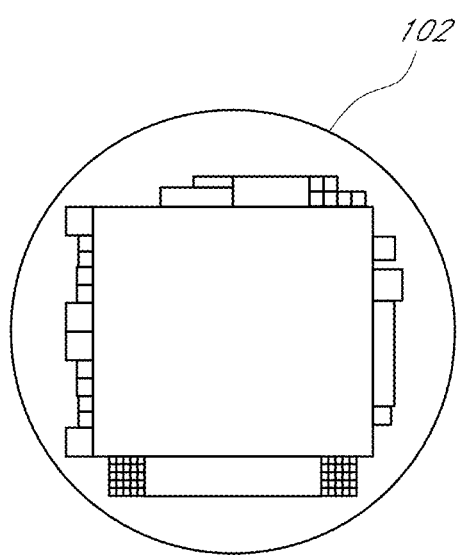
FIG. 26 illustrates an embodiment of a sensor that can detect charged particles.

FIG. 26 illustrates an embodiment of first sensor 102. The first sensor 102 comprises a silicon detector plane embodied as a single printed circuit board. Each first sensor 102 comprises four silicon strip detectors arranged two on each side. Each silicon strip detector is approximately nine centimeters by nine centimeters in size. The front side silicon strip detectors have the strips thereof oriented in a first direction, for example a horizontal direction. The corresponding backside silicon strip detectors have strips oriented in a second direction, for example a perpendicular vertical direction. In other embodiments, the number and sizes of the silicon strip detectors varies and/or other types of detectors may be used.

The strips of the silicon strip detectors comprise relatively narrow doped strips of silicon forming diodes. As previously noted, it is desired that the resolution of the first sensors 102 be relatively high and thus the strips of the silicon strip detectors are preferably formed with widths of approximately 100 µm or less. The diodes of the silicon strip detectors are reversed biased. As incident accelerated protons pass through the strips, ionization currents occur which are detected and measured. By monitoring which of the strips extending in the first direction and in the second direction are activated in unison, a spatial location of the impact of the accelerated proton with the first sensor 102 can be determined. This location information is communicated via the data connection 106 to the data acquisition module 112 for processing by the processor and user interface 114 as previously described.

Figure 27:
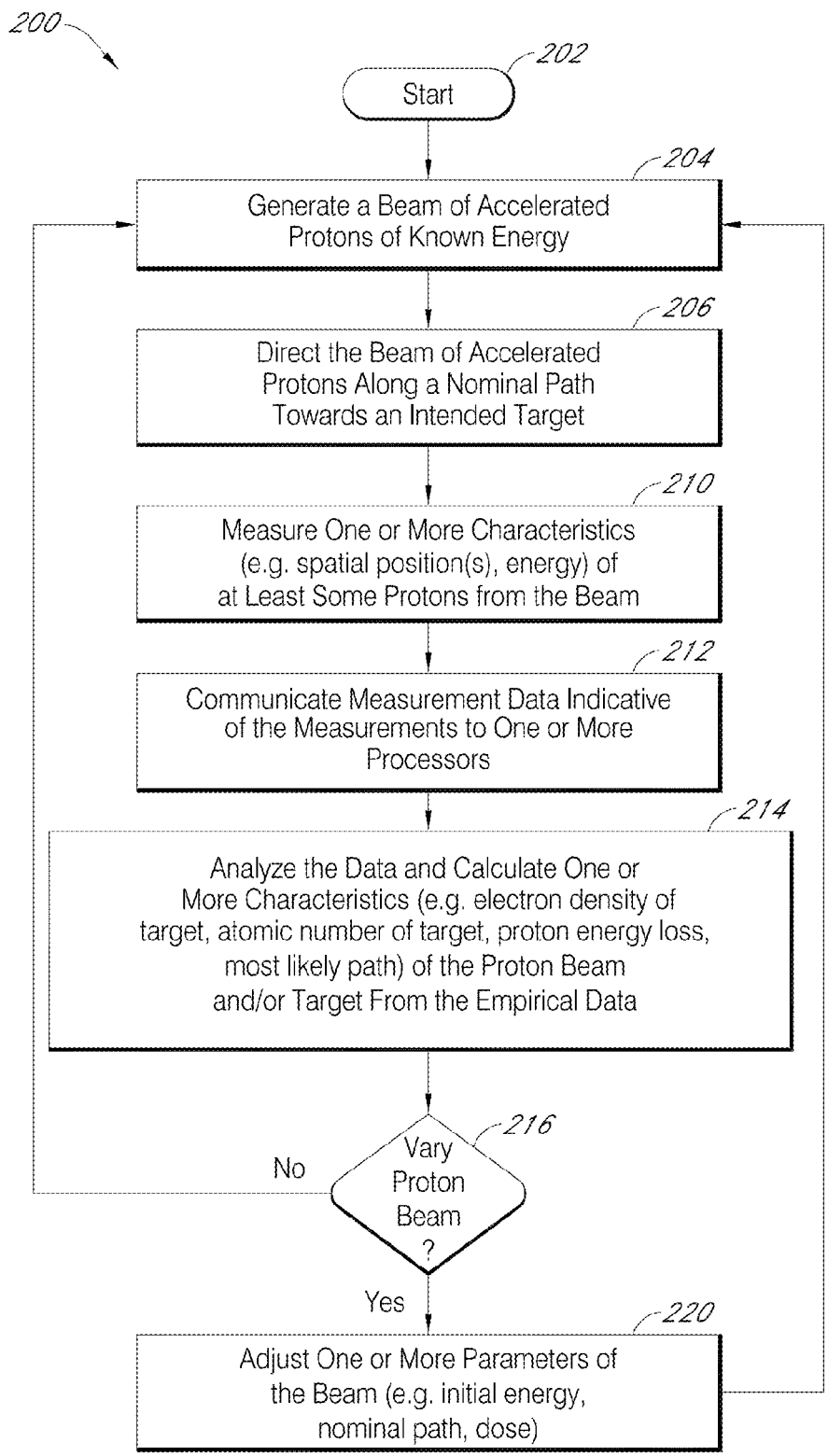
FIG. 27 is a flow chart of embodiments of methods of analyzing a proton beam, for example in a proton therapy system, based on one or more features of the present disclosure.

FIG. 27 is a flow chart illustrating embodiments of methods of analyzing accelerated protons, for example in context of a proton therapy system. The embodiments illustrated and described with respect to FIG. 27 include a variety of features and a variety of subsets of the illustrated and described features can be employed in various embodiments.

The method 200 begins in a start block 202. In embodiments where the method 200 includes therapeutic application of an accelerated proton beam to treat one or more patient conditions, the start block 202 can include an initial diagnosis and treatment plan. For example, the start block 202 can include a clinician evaluating a patient's particular condition and prescribing a treatment plan, for example including doses and energies of a therapeutic proton beam and desired approach vectors. The start block 202 can also include positioning the patient in a desired treatment pose.

In a block 204, a stream of accelerated protons is generated. The generation of accelerated protons in block 204 can include generating protons of a known mean initial energy.

In a block 206, the stream of accelerated protons generated in the block 204 is directed along a nominal path towards an intended target. In some applications, the nominal path is selected such that a Bragg peak of the protons is substantially coincident with a selected region or volume within a patient. It will be understood that the nominal path in order to have a Bragg peak occur at a desired location is dependent on a number of factors including but not limited to focus of the beam, initial beam energy, and material/tissue through which the beam passes.

As previously noted, predicatively estimating an appropriate nominal path and initial beam energy to achieve Bragg peak occurrence at a desired position is problematic and subject to numerous inaccuracies and errors. Embodiments of the method 200 can include the feature of empirical measurements of the interaction between the proton beam and the intended target to allow a clinician to adjust one or more parameters of the proton beam, as indicated, to more accurately achieve the desired interaction between the proton beam and the target.

In a block 210, one or more characteristics of at least some protons from the proton beam are measured. These characteristics can include one or more of spatial positions through which the protons pass, an incident energy of a proton, a translational displacement of a proton from an expected path, and/or an angle of divergence of a proton from an expected path. These measurements can proceed according to any of the previously described embodiments.

The measurements of block 210 result in data that is indicative of the measurements performed in block 210. For example, the measurements of block 210 can result in data, e.g. a digitized word, indicative of a particular measurement and/or for a number of different discreet measurements. In a block 212, the measurement data is communicated to one or more processors. The one or more processors can be local to a proton therapy system and/or can be remotely located. As previously noted, the communication of block 212 can occur in a variety of manners including but not limited to wireless communication, wired communication, fiber optic cables, and the like.

In a block 214, the processors analyze the data and calculate one or more characteristics of the proton beam and/or target from the empirical data obtained in block 210. As previously described, a variety of characteristics of the proton beam and/or the target can be determined based on the observed characteristics of individual protons from the beam. For example, an electron density of tissue/material through which the proton beam has passed can be determined based on the observed characteristics of the individual protons. The electron density is indicative of the material constitution of the target region and can be helpful, for example, in discriminating diseased tissue from healthy tissue.

Similarly, indications of the atomic number of material in the target region can be inferred from the measured characteristics observed in block 210 and can also provide information indicative of the material constitution of the target region. Data from a plurality of protons measured in block 210 can be analyzed to regressively reconstruct a most likely path of the protons and be utilized to empirically calculate an estimation of an actual beam path. If an empirically determined most likely beam path differs from the intended nominal path, a clinician can adjust a proton therapy system to more accurately align an intended nominal path of the proton beam with the desired target. Similarly, if empirical measurements from block 210 indicate that the Bragg peak is not occurring with a desired coincidence with the target region, the clinician can adjust one or both of the nominal path and an initial energy of the proton beam to more accurately align the Bragg peak with the intended location.

Thus, the method 200 can include a decision block 216 where a determination is made whether the proton beam needs to be varied or adjusted. If the determination of block 216 is negative, e.g. that the orientation and initial energy/dose of the proton beam is proceeding within acceptable parameters, the proton beam can continue to be provided under the existing conditions for the duration of the indicated treatment fraction. However, if the determination of decision block 216 is affirmative, a block 220 can be implemented wherein one or more parameters of the beam is adjusted. In some embodiments, any indicated adjustments can be performed in real time, e.g. during a treatment session. In some embodiments, any indicated adjustments can be preformed automatically by the system 100. As previously noted, these parameters can include one or more of an initial energy, a nominal path or spatial vector, and/or a treatment dose. Proceeding from a negative determination of block 216 or from block 220, the method 200 would generally iterate sequentially through blocks 204, 206, 210, 212, 214, and 216 as previously described through the duration of the treatment session.

Conditional language, such as, among others terms, "can," "could," "might," or "may," and "preferably," unless specifically stated otherwise, or otherwise understood within the context as used, is generally intended to convey that certain embodiments include, while other embodiments do not include, certain features, elements and/or steps.

Many variations and modifications can be made to the above-described embodiments, the elements of which are to be understood as being among other acceptable examples. Thus, the foregoing description is not intended to limit the scope of protection.

What is claimed is:

1. A method for monitoring proton therapy, the method comprising:
    positioning a patient along a beam path;
    delivering a plurality of protons along the beam path to the patient;
    detecting interactions of at least some of the plurality of protons delivered to the patient, the detected interactions comprising scattering locations of protons from within the patient, the detected interactions providing information about numbers of scattering protons at the scattering locations, wherein detecting interactions comprises detecting the protons scattered at an angle relative to the beam path, the scattering angle relative to the beam path being within a range of approximately 20 degrees to 90 degrees; and
    estimating a dose deposited for the plurality of protons based on the numbers of scattering protons at the scattering locations.

2. The method of claim 1, wherein the angle is within a range of approximately 25 degrees to 70 degrees.

3. The method of claim 2, wherein the angle is within a range of approximately 30 degrees to 60 degrees.

4. The method of claim 3, wherein the angle is approximately 45 degrees.

5. The method of claim 1, wherein a beam comprising the plurality of protons has an average kinetic energy in a range of approximately 45 MeV to 300 MeV.

6. The method of claim 5, wherein a beam comprising the plurality of protons has an average kinetic energy in a range of approximately 80 MeV to 270 MeV.

7. The method of claim 6, wherein a beam comprising the plurality of protons is configured for cancer therapy based on a Bragg peak effect.

8. The method of claim 7, wherein a beam comprising the plurality of protons has an average kinetic energy of approximately 100 MeV.

9. The method of claim 6, wherein a beam comprising the plurality of protons is configured for radiosurgery application based on ionization by the protons.

10. The method of claim 9, wherein a beam comprising the plurality of protons has an average kinetic energy of approximately 250 MeV.

11. The method of claim 1, wherein the detecting of the interactions comprises characterizing tracks associated with the interactions with one or more silicon strip detectors and a proton calorimeter.

12. The method of claim 1, wherein the detecting of the interactions comprises characterizing tracks associated with the interactions on a plurality of sides about the beam path.

13. The method of claim 12, wherein the tracks associated with the interactions are characterized at two opposing sides substantially symmetrical about the beam path.

14. The method of claim 1, further comprising:
    adjusting the scattering angle relative to the beam path at which the protons are detected; and
    detecting interactions of at least some of the protons delivered to the patient at the adjusted scattering angle.

15. The method of claim 1, further comprising positioning a detector assembly to detect protons scattered at the scattering angle.

16. The method of claim 1, further comprising detecting scattering locations of protons from within the patient at a second scattering angle relative to the beam path, the second scattering angle different from the scattering angle.

17. The method of claim 16, further comprising positioning a second detector assembly to detect protons scattered at the second scattering angle.

18. The method of claim 12, wherein characterizing tracks associated with the interactions comprises generating interaction profiles.

* * * * *